United States Patent
Kuroyanagi et al.

(10) Patent No.: US 7,928,283 B2
(45) Date of Patent: Apr. 19, 2011

(54) TRANSGENIC REPORTER SYSTEM THAT REVEALS EXPRESSION PROFILES AND REGULATION MECHANISMS OF ALTERNATIVE SPLICING IN NEMATODES

(75) Inventors: Hidehito Kuroyanagi, Tokyo (JP); Masatoshi Hagiwara, Tokyo (JP)

(73) Assignee: Kinopharma, Inc., Tokyo (JP)

( * ) Notice: Subject to any disclaimer, the term of this patent is extended or adjusted under 35 U.S.C. 154(b) by 560 days.

(21) Appl. No.: 11/904,094

(22) Filed: Sep. 26, 2007

(65) Prior Publication Data

US 2008/0095712 A1    Apr. 24, 2008

Related U.S. Application Data

(60) Provisional application No. 60/847,409, filed on Sep. 27, 2006.

(51) Int. Cl.
*G01N 33/00* (2006.01)
*A01K 67/00* (2006.01)
(52) U.S. Cl. .................................. 800/3; 800/8
(58) Field of Classification Search .................. None
See application file for complete search history.

(56) References Cited

OTHER PUBLICATIONS

Cameron, E.R. Recent Advances in Transgenic Techology, Molec. Biotech. 1997, vol. 7, pp. 253-265.*
Sigmund, C.D. Viewpoint: Are Studies in Genetically Altered Mice Out of Control. Arteroscler. Throm. Vasc. Biol. 2000, vol. 20, pp. 1425-1429.*
Niemann, H. Transgenic Farm Animals Get Off the Ground. Transg. Res. 1998, vol. 7, pp. 73-75.*
Smith. Gene Transfer in Higher Animals: Theoretical Considerations and Key Concepts. J. Biotech. 2002, vol. 99, pp. 1-22.*
Montoliu. Gene Transfer Strategies in Animal Transgenesis. Cloning and Stem Cells. 2002, vol. 4, pp. 39-46.*
Ristevski. Making Better Transgenic Models. Molecular Biotechnology, vol. 29, pp. 153-163.*
Prelle et al. Establishment of Pluripotent Cell Lines from Vertebrate Sprecies-Present Status and Future Prospects. Cells Tissues Organs, 1989, vol. 165, pp. 220-236.*

* cited by examiner

*Primary Examiner* — Deborah Crouch
(74) *Attorney, Agent, or Firm* — Carmody & Torrance LLP

(57) ABSTRACT

An object of the present invention is to develop a new alternative splicing reporter system and to provide a method for detecting alternative splicing patterns in a multicellular organism more precisely, a method for identifying efficiently substances and gene regions that affect alternative splicing in a multicellular organism, and the like by utilizing the alternative splicing reporter system. Specifically, the present invention relates to a method for detecting alternative splicing in a multicellular organism, and a method for identifying substances and gene regions that affect alternative splicing in a multicellular organism, which use a DNA construct in which at least two different reporter genes are inserted into a specific gene that undergoes alternative splicing, or a combination of DNA constructs (a combination of at least two different DNA constructs) in which DNA construct a reporter gene is inserted into a specific gene that undergoes alternative splicing.

8 Claims, 11 Drawing Sheets
(11 of 11 Drawing Sheet(s) Filed in Color)

Fig. 1
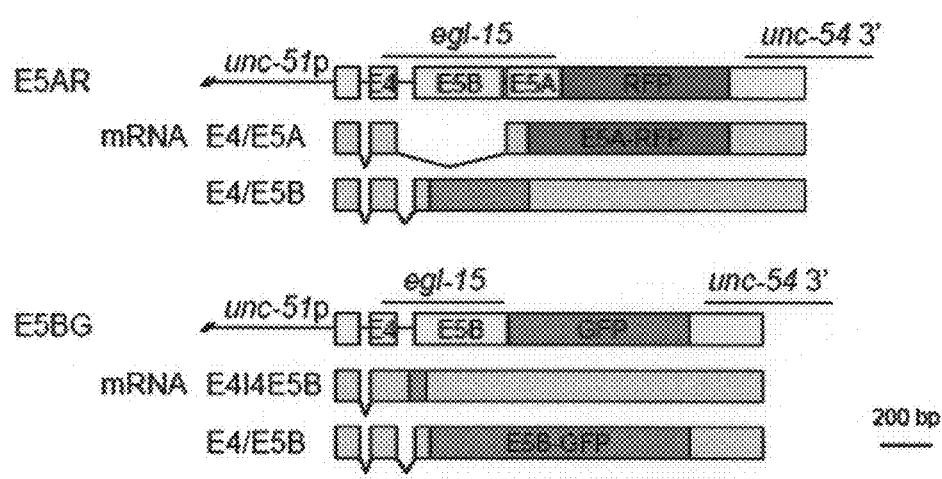
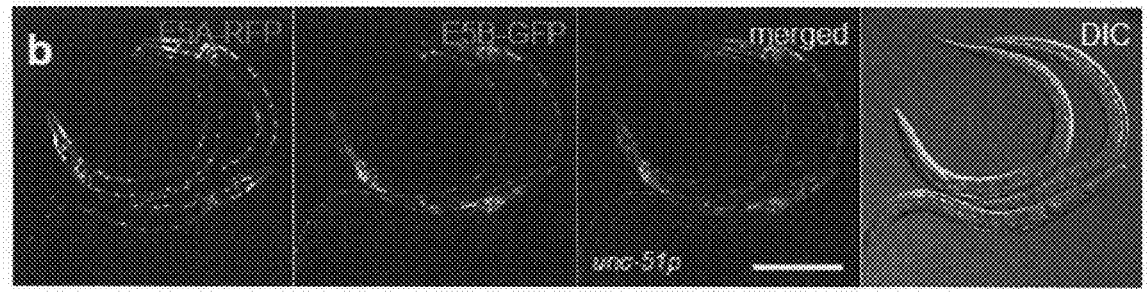

Fig. 2
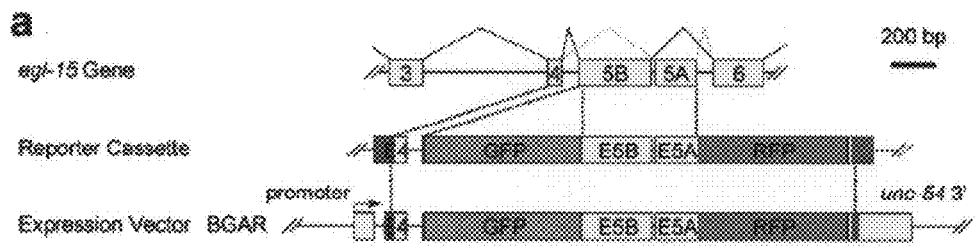
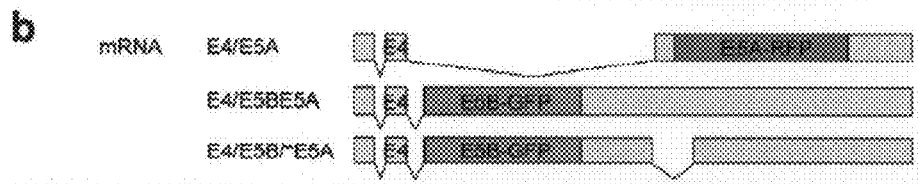
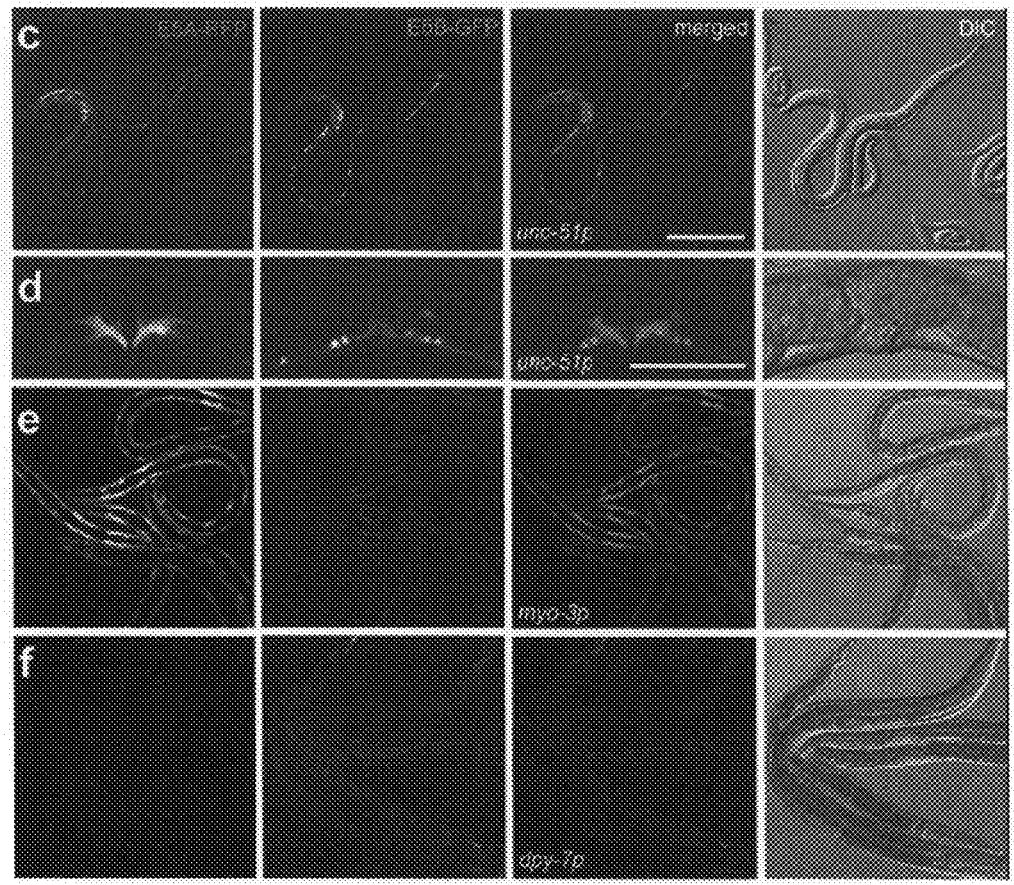
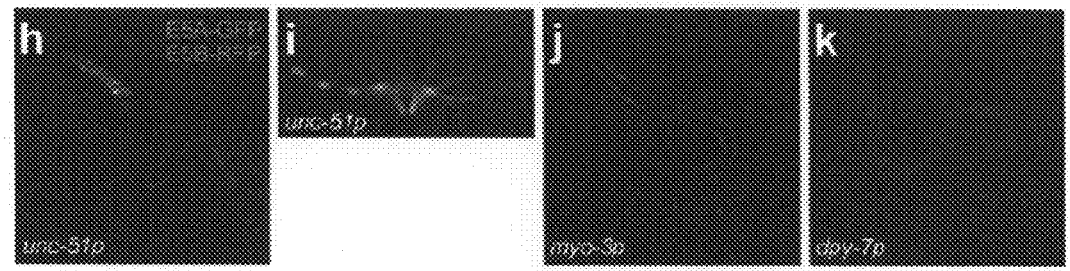

Fig. 8
a
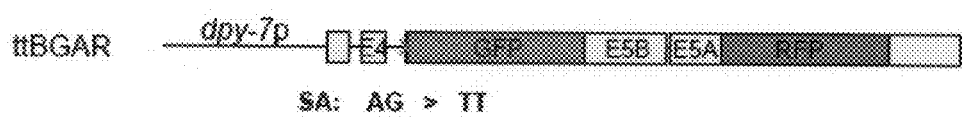
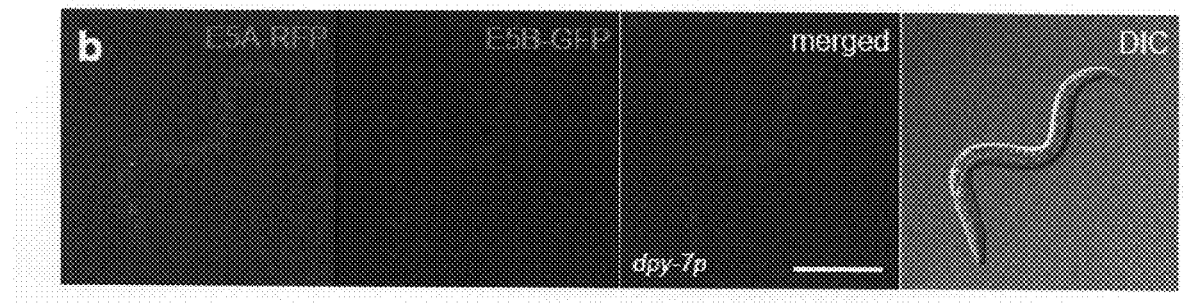

Fig. 9
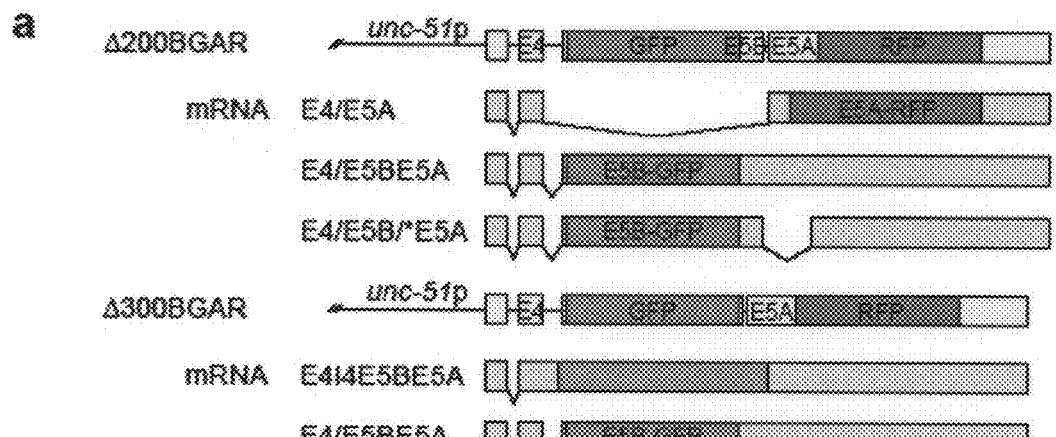
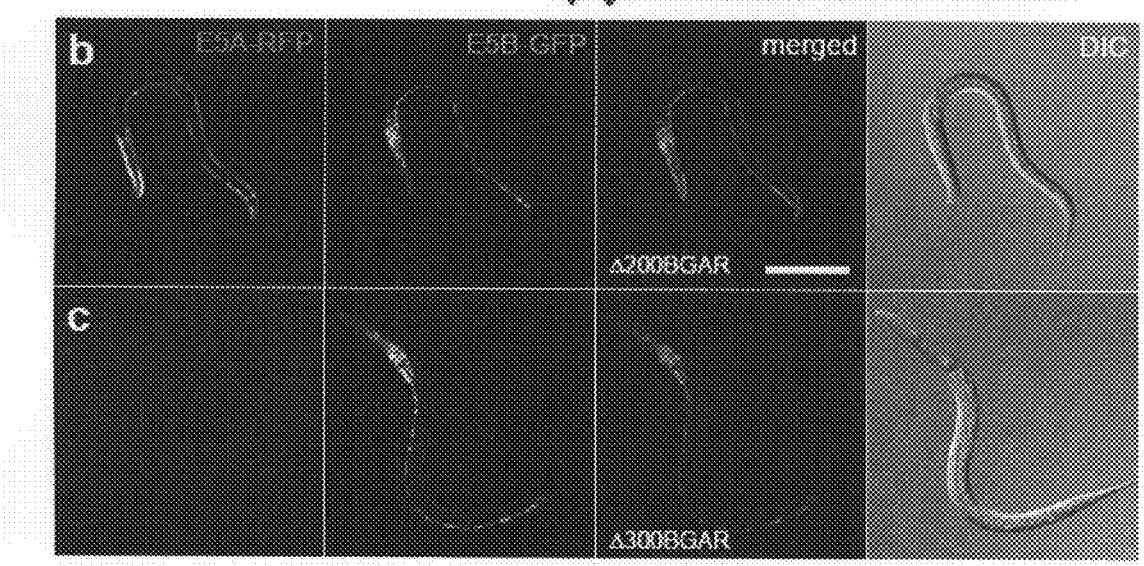

Fig.11
wildtype
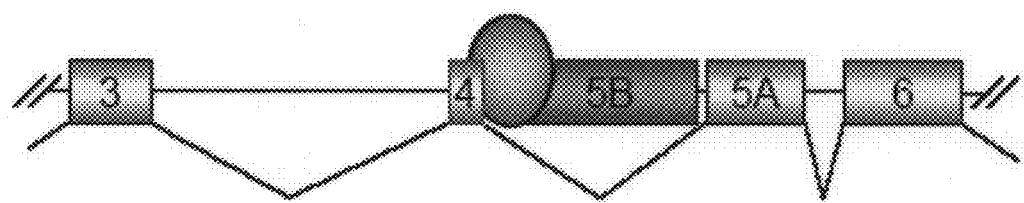
asd-1; fox-1 mutant
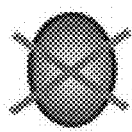
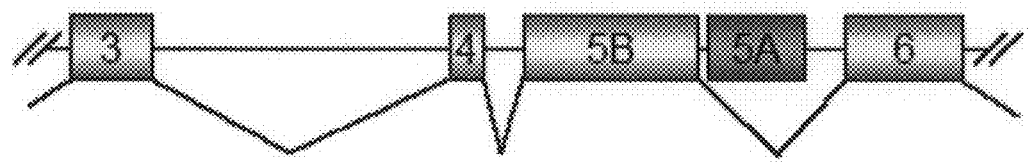

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Artificial Sequence for Primer

<400> SEQUENCE: 1
gtctctagac gtacacaacg catctggaca                                      30

<210> SEQ ID NO 2
<211> LENGTH: 33
<212> TYPE: DNA
<213> ORGANISM: Artificial Sequence
<220> FEATURE:

<223> OTHER INFORMATION: Artificial Sequence for Primer

<400> SEQUENCE: 2
caaagatctg aaaacaaagc acaccatssa tgg                33

<210> SEQ ID NO 3
<211> LENGTH: 30
<212> TYPE: DNA
<213> ORGANISM: Artificial Sequence
<220> FEATURE:
<223> OTHER INFORMATION: Artificial Sequence for Primer

<400> SEQUENCE: 3
tgaagcggcc gctggaatgt gtttgtttat                30

<210> SEQ ID NO 4
<211> LENGTH: 30
<212> TYPE: DNA
<213> ORGANISM: Artificial Sequence
<220> FEATURE:
<223> OTHER INFORMATION: Artificial Sequence for Primer

<400> SEQUENCE: 4
gcggatccaa aggatgattg atctgtctta                30

TRANSGENIC REPORTER SYSTEM THAT REVEALS EXPRESSION PROFILES AND REGULATION MECHANISMS OF ALTERNATIVE SPLICING IN NEMATODES

RELATED U.S. APPLICATION DATA

This application claims the benefit of U.S. Provisional Application No. 60/847,409, filed Sept. 27, 2006.

This application incorporates by reference the material contained on the compact disc submitted herewith. The disc contains the file entitled SEQUENCE LISTING, which was created on Sept. 20, 2007.

BACKGROUND OF THE INVENTION

1. Field of the Invention

The present invention relates to a method for detecting alternative splicing in a multicellular organism, a method for identifying substances and gene regions that affect alternative splicing in a multicellular organism, and the like, which utilize a new alternative splicing reporter system developed by the present inventors.

2. Description of the Related Art

Alternative splicing of pre-mRNAs enables multicellular organisms to create a huge diversity of proteomes from a finite number of genes. Many alternative splicing events have been shown to be regulated in cell-type-dependent and/or developmentally regulated manners. However, extensive studies in vitro or in cultured cells have not fully elucidated the regulation mechanisms that determine the specific splicing patterns in living organisms.

The importance of the alternative splicing of pre-mRNAs on the structure and function of proteins, as well as on cellular processes, has been well discussed (Black, D. L. Protein diversity from alternative splicing: a challenge for bioinformatics and post-genome biology. Cell 103, 367-370 (2000).; Maniatis, T. & Tasic, B. Alternative pre-mRNA splicing and proteome expansion in metazoans. Nature 418, 236-243 (2002).; Stamm, S. et al. Function of alternative splicing. Gene 344, 1-20 (2005).). Recent global studies on cDNA sequences or microarray data have predicted that as many as two thirds of human genes have multiple isoforms of mature mRNAs (Modrek, B. & Lee, C. A genomic view of alternative splicing. Nat Genet. 30, 13-19 (2002).; Eyras, E., Caccamo, M., Curwen, V. & Clamp, M. ESTGenes: alternative splicing from ESTs in Ensembl. Genome Res 14, 976-987 (2004).; Kampa, D. et al. Novel RNAs identified from an in-depth analysis of the transcriptome of human chromosomes 21 and 22. Genome Res 14, 331-342 (2004).), and the utilization of alternative splicing microarrays revealed that many alternative splicing events are controlled in tissue- and cell-type and/or developmental-stage dependent manners (Johnson, J. M. et al. Genome-wide survey of human alternative pre-mRNA splicing with exon junction microarrays. Science 302, 2141-2144 (2003).; Pan, Q. et al. Revealing global regulatory features of mammalian alternative splicing using a quantitative microarray platform. Mol Cell 16, 929-941 (2004).). These facts indicate that unidentified "cellular codes" underlie the regulation of alternative splicing of so many genes in living organisms (Sharp, P. A. The discovery of split genes and RNA splicing. Trends Biochem Sci 30, 279-281 (2005).; Shin, C. & Manley, J. L. Cell signalling and the control of pre-mRNA splicing. Nat Rev Mol Cell Biol 5, 727-738 (2004).; Hagiwara, M. Alternative splicing: a new drug target of the post-genome era. Biochim Biophys Acta 1754, 324-331 (2005).; Matlin, A. J., Clark, F. & Smith, C. W. Understanding alternative splicing: towards a cellular code. Nat Rev Mol Cell Biol 6, 386-398 (2005).; Fu, X. D. Towards a splicing code. Cell 119, 736-738 (2004).). Experimental elucidation of the expression profiles and regulation mechanisms of alternative splicing would lead to a better understanding of genome functions and the cellular identities of multicellular organisms.

Regulation mechanisms of alternative splicing have been experimentally studied mostly in vitro and in cultured cells (Blencowe, B. J. Exonic splicing enhancers: mechanism of action, diversity and role in human genetic diseases. Trends Biochem Sci 25, 106-110 (2000).; Hastings, M. L. & Krainer, A. R. Pre-mRNA splicing in the new millennium. Curr Opin Cell Biol 13, 302-309 (2001).). General cis-acting enhancer and silencer elements and trans-acting factors, involved in the regulation of both constitutive and alternative exons, have been well characterized by analyzing model genes. Expression cloning strategies have enabled the global collection of putative sequence elements that function in cultured cells and bioinformatic analyses have identified putative cis-elements within exons and introns.

Recently, however, conditional knockouts of trans-acting SR protein families revealed that alternative splicing of only a few target genes are crucially dependent on a specific protein in cardiac muscles, even though many more genes expressed in this tissue have typical cis-elements (Xu, X. et al. ASF/SF2-regulated CaMKIIdelta alternative splicing temporally reprograms excitation-contraction coupling in cardiac muscle. Cell 120, 59-72 (2005).). This indicates that we cannot precisely predict the alternative splicing patterns in each tissue or cell without the assessment of the regulation mechanisms in living organisms.

BRIEF SUMMARY OF THE INVENTION

An object of the present invention is to solve conventional problems and to attain the following object. Specifically, an object of the present invention is to develop a new alternative splicing reporter system and to provide a method for detecting alternative splicing patterns in a multicellular organism more precisely, a method for identifying efficiently substances and gene regions that affect alternative splicing in a multicellular organism, and the like by utilizing the alternative splicing reporter system.

Some cell-type specific trans-acting alternative splicing factors and their target genes have been identified in conventional genetic studies on *Caenorhabditis elegans* (*C. elegans*) and *Drosophila* (Lundquist, E. A. et al. The mec-8 gene of *C. elegans* encodes a protein with two RNA recognition motifs and regulates alternative splicing of unc-52 transcripts. Development 122, 1601-1610 (1996).; Lisbin, M. J., Qiu, J. & White, K. The neuron-specific RNA-binding protein ELAV regulates neuroglian alternative splicing in neurons and binds directly to its pre-mRNA. Genes Dev 15, 2546-2561 (2001).), suggesting feasibility of genetic approach for comprehensive studies on regulation of alternative splicing. Like in vertebrates, most genes in *C. elegans* have introns (Sakharkar, M. K. & Kangueane, P. Genome SEGE: a database for 'intronless' genes in eukaryotic genomes. BMC Bioinformatics 5, 67 (2004).), and approximately 5% of protein-coding genes have multiple forms of their corresponding mature mRNAs (Nagasaki, H., Arita, M., Nishizawa, T., Suwa, M. & Gotoh, O, Species-specific variation of alternative splicing and transcriptional initiation in six eukaryotes. Gene 364, 53-62 (2005).). In the present invention, because of its advantage in morphological and genetic studies, the present inventors intended to generate a transgenic reporter system by utilizing

*C. elegans*, which enabled to monitor the expression profiles of alternatively spliced exons at a single-cell resolution. Here, the present inventors demonstrate that this system provides us with a clue to identify regulators of alternative splicing patterns.

Specifically, in the present invention, transgenic reporter worms are reported that visualize the expression profiles of each of the mutually exclusive exons. Reporters for exons 5A and 5B of the egl-15 gene showed tissue-specific expression patterns. A fluorescence-assisted worm sorter allowed efficient screening for mutants defective in the tissue-specificity, and the present inventors identified a novel gene, asd-1 (alternative splicing defective-1), which encoded an RNA-binding protein of evolutionarily conserved Fox-1 family. The transgenic reporter system also allowed the identification of a cis-element. Furthermore, an asd-1; fox-1 double mutant was defective in expression of endogenous egl-15 (5A) and phenocopied egl-15 (5A) mutant. This transgenic reporter worm system can be a powerful experimental tool for the comprehensive study of expression profiles and regulation mechanisms of alternative splicing in metazoan.

The present invention is based on the above-mentioned experiences or discoveries by the present inventors, and means for solving the above-mentioned problems are as follows. Specifically, A first method for detecting an alternative splicing of a specific gene in a multicellular organism of the present invention includes:

(a) introducing into the multicellular organism a DNA construct such that at least two different reporter genes are inserted into the specific gene which undergoes the alternative splicing, wherein the reporter genes are inserted so that transcripts of the different reporter genes are each fused with each of at least two different mature mRNAs generated by alternative splicing; and (b) detecting the alternative splicing of the specific gene in the multicellular organism by the expression of the reporter genes.

A first method for testing whether or not a compound to be tested affects an alternative splicing of a specific gene of the present invention includes:

(a) introducing into a multicellular organism a DNA construct such that at least two different reporter genes are inserted into the specific gene which undergoes the alternative splicing, wherein the reporter genes are inserted so that transcripts of the different reporter genes are each fused with each of at least two different mature mRNAs generated by the alternative splicing;

(b) allowing the multicellular organism to contact the compound to be tested;

(c) detecting the alternative splicing of the specific gene in the multicellular organism by the expression of the reporter genes; and (d) determining whether or not the expression of the reporter genes detected in the (c) has changed compared to the expression of the reporter genes in a control which is not allowed to contact the compound to be tested.

A first method for identifying a gene region affecting an alternative splicing of a specific gene of the present invention includes:

(a) introducing into a multicellular organism a DNA construct such that at least two different reporter genes are inserted into the specific gene which undergoes the alternative splicing, wherein the reporter genes are inserted so that transcripts of the different reporter genes are each fused with each of at least two different mature mRNAs generated by the alternative splicing;

(b) treating the multicellular organism with a mutagen;

(c) detecting the alternative splicing of the specific gene in the multicellular organism by the expression of the reporter genes;

(d) selecting an individual in which the expression of the reporter genes detected in the (c) has changed compared to the expression of the reporter genes in a control which is not subjected to the mutagen treatment; and (e) identifying a mutated gene region in the individual.

A first method for identifying a region in a specific gene affecting an alternative splicing of the specific gene of the present invention includes:

(a) introducing into a multicellular organism a DNA construct such that at least two different reporter genes are inserted into the specific gene into which a mutation has been introduced and which undergoes the alternative splicing, wherein the reporter genes are inserted so that transcripts of the different reporter genes are each fused with each of at least two different mature mRNAs generated by the alternative splicing;

(b) detecting the alternative splicing of the specific gene in the multicellular organism by the expression of the reporter genes; and (c) determining whether or not the expression of the reporter genes detected in the (b) has changed compared to the expression of the reporter genes in a control in which a mutation has not been introduced into the specific gene.

A second method for detecting an alternative splicing of a specific gene in a multicellular organism of the present invention includes:

(a) introducing into the multicellular organism a combination of DNA constructs, wherein in the DNA construct, a reporter gene is inserted into the specific gene which undergoes the alternative splicing, and the combination of DNA constructs satisfies all of the following conditions (i) to (iv):

(i) reporter genes inserted into each DNA construct are different from each other, (ii) in each DNA construct, the reporter gene is inserted into the specific gene so that a transcript of the reporter gene is fused with a plurality of mature mRNAs generated by the alternative splicing, (iii) a transcript portion of the reporter gene in only one mature mRNA of the plurality of mature mRNAs generated by the alternative splicing from each DNA construct is translated in a correct reading frame, and (iv) only when a specific splicing is selected among alternative splicing patterns, the translation in a correct reading frame is induced in each DNA construct, and the specific splicing which induces the translation in a correct reading frame is different depending on each DNA construct; and (b) detecting the alternative splicing of the specific gene in the multicellular organism by the expression of the reporter genes.

A second method for testing whether or not a compound to be tested affects an alternative splicing of a specific gene of the present invention includes:

(a) introducing into a multicellular organism a combination of DNA constructs, wherein in the DNA construct, a reporter gene is inserted into the specific gene which undergoes the alternative splicing, and the combination of DNA constructs satisfies all of the following conditions (i) to (iv):

(i) reporter genes inserted into each DNA construct are different from each other, (ii) in each DNA construct, the reporter gene is inserted into the specific gene so that a transcript of the reporter gene is fused with a plurality of mature mRNAs generated by the alternative splicing, (iii) a transcript portion of the reporter gene in only one mature mRNA of the plurality of mature mRNAs generated by the alternative splicing from each DNA construct is translated in a correct reading frame, and (iv) only when a specific splicing is selected among alternative splicing patterns, the translation in a correct reading frame is induced in each DNA construct, and the specific splicing which induces the translation in a correct reading frame is different depending on each DNA construct;

(b) allowing the multicellular organism to contact the compound to be tested;

(c) detecting the alternative splicing of the specific gene in the multicellular organism by the expression of the reporter genes; and (d) determining whether or not the expression of the reporter genes detected in the (c) has changed compared to the expression of the reporter genes in a control which is not allowed to contact the compound to be tested.

A second method for identifying a gene region affecting an alternative splicing of a specific gene of the present invention includes:

(a) introducing into a multicellular organism a combination of DNA constructs, wherein in the DNA construct, a reporter gene is inserted into the specific gene which undergoes the alternative splicing, and the combination of DNA constructs satisfies all of the following conditions (i) to (iv):

(i) reporter genes inserted into each DNA construct are different from each other, (ii) in each DNA construct, the reporter gene is inserted into the specific gene so that a transcript of the reporter gene is fused with a plurality of mature mRNAs generated by the alternative splicing, (iii) a transcript portion of the reporter gene in only one mature mRNA of the plurality of mature mRNAs generated by the alternative splicing from each DNA construct is translated in a correct reading frame, and (iv) only when a specific splicing is selected among alternative splicing patterns, the translation in a correct reading frame is induced in each DNA construct, and the specific splicing which induces the translation in a correct reading frame is different depending on each DNA construct;

(b) treating the multicellular organism with a mutagen;

(c) detecting the alternative splicing of the specific gene in the multicellular organism by the expression of the reporter genes;

(d) selecting an individual in which the expression of the reporter genes detected in the (c) has changed compared to the expression of the reporter genes in a control which is not subjected to the mutagen treatment; and (e) identifying a mutated gene region in the individual.

A second method for identifying a region in a specific gene affecting an alternative splicing of the specific gene of the present invention includes:

(a) introducing into a multicellular organism a combination of DNA constructs, wherein in the DNA construct, a reporter gene is inserted into the specific gene into which a mutation has been introduced and which undergoes the alternative splicing, and the combination of DNA constructs satisfies all of the following conditions (i) to (iv):

(i) reporter genes inserted into each DNA construct are different from each other, (ii) in each DNA construct, the reporter gene is inserted into the specific gene so that a transcript of the reporter gene is fused with a plurality of mature mRNAs generated by the alternative splicing, (iii) a transcript portion of the reporter gene in only one mature mRNA of the plurality of mature mRNAs generated by the alternative splicing from each DNA construct is translated in a correct reading frame, and (iv) when a specific splicing is selected among alternative splicing patterns, the translation in a correct reading frame is induced in each DNA construct, and the specific splicing which induces the translation in a correct reading frame is different depending on each DNA construct;

(b) detecting the alternative splicing of the specific gene in the multicellular organism by the expression of the reporter genes; and (c) determining whether or not the expression of the reporter genes detected in the (b) has changed compared to the expression of the reporter genes in a control in which a mutation has not been introduced into the specific gene.

The present invention can solve conventional problems, can attain the above-mentioned object, and can provide a method for detecting alternative splicing patterns in a multicellular organism, a method for identifying efficiently substances and gene regions that affect alternative splicing in a multicellular organism, and the like.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 1 depicts alternative splicing reporter worms with separate mini-genes (i.e., having a mini-gene in which cDNA for RFP is introduced downstream of exon 5A, and a mini-gene in which cDNA for GFP is introduced downstream of exon 5B).

FIG. 2 depicts alternative splicing reporter worms with unified mini-genes in which cDNAs for RFP and GFP were introduced downstream of exon 5A and upstream of exon 5B, respectively.

FIG. 8 shows that inactivation of E5B-GFP leads to selection of E5A-RFP in hypodermis.

FIG. 9 shows that exon 5B sequence is not required for inclusion or suppression of E5B-GFP.

FIG. 11 is a diagram showing a model of regulation of endogenous egl-15 exon 5s in sex myoblasts.

Figure 3:
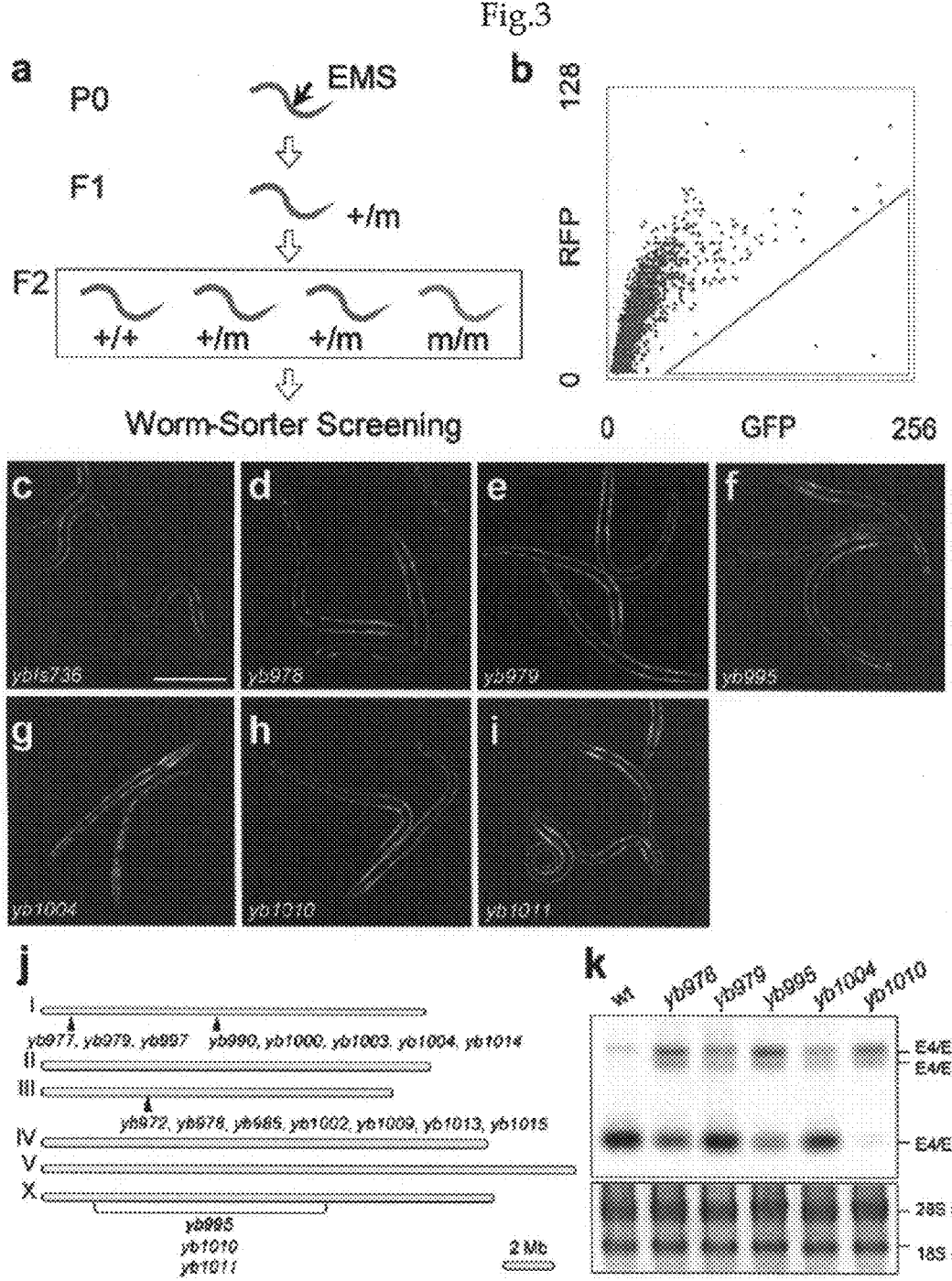
FIG. 3 depicts Screening for mutants defective in tissue-specific alternative splicing of egl-15 reporter.

DETAILED DESCRIPTION OF THE INVENTION (First and Second Alternative Splicing Reporter Systems)

In a first aspect, the present invention relates to an alternative splicing reporter system in a multicellular organism using a DNA construct in which at least two different reporter genes are inserted into a specific gene that undergoes alternative splicing (for example, see FIG. 2A). In a second aspect, the present invention relates to an alternative splicing reporter system in a multicellular organism using a combination of DNA constructs (a combination of at least two different DNA constructs) in which DNA construct a reporter gene is inserted into a specific gene that undergoes alternative splicing (for example, see FIG. 1A).

Both of the first and second systems allows the detection of alternative splicing patterns of a specific gene in vivo in multicellular organisms by introducing a DNA construct (or combination of DNA constructs), into which at least two different reporter genes are inserted in total, into a multicellular organism. The first and second systems each can be suitably utilized for "(1) a method for detecting alternative splicing of a specific gene in a multicellular organism", "(2) a method for testing whether or not a compound to be tested affects alternative splicing of a specific gene", "(3) a method for identifying a gene region affecting alternative splicing of a specific gene", and "(4) a method for identifying a region in a specific gene affecting alternative splicing of the specific gene" of the present invention, which will be described later.

It was difficult to precisely predict tissue-specific and/or stage-specific alternative splicing patterns in vivo from the results of conventional in vitro studies on alternative splicing using cultured cells, etc. Use of the first and second systems enables direct and accurate detection of tissue-specific and/or stage-specific alternative splicing patterns in vivo in multicellular organisms Thus, it is considered that the first and second systems can become powerful experimental tools for elucidating mechanisms of alternative splicing in multicellular organisms.

<Multicellular Organism>

In the first and second systems, the "multicellular organism" is not particularly limited and can be appropriately selected depending on the application as long as it consists of many cells and has mechanisms of alternative splicing, including, for example, animals, plants, and fungus. The animal may be a vertebrate or an invertebrate, but *Caenorhabditis elegans* (*C. elegans*) is preferable. The *C. elegans* is an invertebrate and belongs to nematoda. Since *C. elegans* has been established as a model organism, it is easy to handle. In addition, *C. elegans* has a transparent body, enabling easy detection of the expression of reporter gene. Like in vertebrates, most genes in *C. elegans* have introns (Sakharkar, M. K. & Kangueane, P. Genome SEGE: a database for 'intronless' genes in eukaryotic genomes. BMC Bioinformatics 5, 67 (2004).), and approximately 5% of protein-coding genes have multiple forms of their corresponding mature mRNAs (Nagasaki, H., Arita, M., Nishizawa, T., Suwa, M. & Gotoh, O, Species-specific variation of alternative splicing and transcriptional initiation in six eukaryotes. Gene 364, 53-62 (2005).). Since *C. elegans* has relatively small introns and the regulation mechanisms of alternative splicing are expected to be simple, it is considered that use of *C. elegans* helps to reveal basic rules of regulation mechanisms of alternative splicing in higher eukaryotes.

<Specific Gene Undergoing Alternative Splicing>

The "specific gene that undergoes alternative splicing" (hereinafter, may be simply referred to as "specific gene") in the first and second systems is not particularly limited and can be appropriately selected depending on the application as long as it is a gene of multicellular organisms and can produce multiple isoforms of mature mRNAs consisting of different combinations of exons as a result of alternative splicing. Examples thereof include egl-15 gene in *C. elegans*, and the like. The egl-15 gene encodes a sole homolog of fibroblast growth factor receptor (FGFR) in *C. elegans* and contains exons 5A and 5B which are selected mutually exclusively in alternative splicing (Goodman, S. J., Branda, C. S., Robinson, M. K., Burdine, R. D. & Stern, M. J. Alternative splicing affecting a novel domain in the *C. elegans* EGL-15 FGF receptor confers functional specificity. Development 130, 3757-3766 (2003).). Here, the "alternative splicing" refers to a phenomenon in which multiple isoforms of mature mRNAs consisting of different combinations of exons are produced in cells by varying patterns of splicing when introns are removed from pre-mRNAs by RNA splicing. This phenomenon enables organisms having alternative splicing machinery to produce different proteins from a single gene.

<Reporter Gene>

In the first and second systems, the "reporter gene" is not particularly limited and can be appropriately selected depending on the application. Examples of the reporter gene include fluorescent protein genes such as a green fluorescent protein (GFP) and a red fluorescent protein (RFP), enzyme genes that catalyze chromogenic reaction or color-developing reaction, or luminous reaction, and the like. In the first and second systems, at least two different reporter genes are used in total. The combination thereof is not particularly limited and can be appropriately selected depending on the application as long as their expressions can be distinguished from each other based on the difference of fluorescence or developed color. For example, a combination of a green fluorescent protein (GFP) and a red fluorescent protein (RFP), and the like can be suitably used.

<DNA Construct>

—DNA Construct of First System—

The DNA construct in the first system is one in which at least two different reporter genes are inserted into a specific gene that undergoes alternative splicing. The at least two different reporter genes are inserted into the specific gene such that transcripts of the at least two different reporter genes are each fused with each of at least two different mature mRNAs generated by alternative splicing of the specific gene.

Preferably, the at least two different reporter genes are each connected to a different exon which is included in at least two different transcripts (mature mRNAs) generated by alternative splicing of the specific gene (for example, see FIGS. 2A and 2B). Each reporter gene may be connected upstream (5' side) of each of the exons, or may be connected downstream (3' side) thereof; however, each reporter gene is required to be connected to each of the exons such that each reporter gene is translated in a correct reading frame only when each exon, to which each reporter gene is connected, is translated in a correct reading frame. Such structure of the DNA construct allows to check whether each exon, to which each reporter gene is connected, has been translated in a correct reading frame when the expression of each reporter gene is detected. That is, analysis of respective expression patterns of the at least two different reporter genes makes it possible to check alternative splicing patterns of the specific gene comprehensively.

—DNA Construct of Second System—

On the other hand, the DNA construct in the second system is one in which a reporter gene is inserted into a specific gene that undergoes alternative splicing. The second system is characterized in that a combination of such DNA constructs (combination of at least two different DNA constructs) is used. Here, the combination of DNA constructs satisfies all conditions of the following (i) to (iv):

(i) reporter genes inserted into each DNA construct are different from each other;

(ii) in each DNA construct, the reporter gene is inserted into the specific gene so that a transcript of the reporter gene is fused with a plurality of mature mRNAs generated by the alternative splicing;

(iii) a transcript portion of the reporter gene in only one mature mRNA of the plurality of mature mRNAs generated by the alternative splicing from each DNA construct is translated in a correct reading frame; and (iv) only when a specific splicing is selected among alternative splicing patterns, the translation in a correct reading frame is induced in each DNA construct, and the specific splicing which induces the translation in a correct reading frame is different depending on each DNA construct.

Preferably, each reporter gene in each DNA construct is connected to one of different exons which are included in at least two different transcripts (mature mRNAs) generated by alternative splicing of the specific gene (for example, see FIG. 1A). Each reporter gene may be connected upstream (5' side) of each of the exons, or may be connected downstream (3' side) thereof; however, each reporter gene is required to be connected to each of the exons such that each reporter gene is translated in a correct reading frame only when each exon, to which each reporter gene is connected, is translated in a correct reading frame. Use of combination of DNA constructs constructed in such a way allows to check whether each exon, to which each reporter gene is connected, has been translated in a correct reading frame when the expression of each reporter gene is detected. That is, analysis of each expression pattern of each reporter gene in the combination of DNA constructs makes it possible to check alternative splicing patterns of the specific gene comprehensively.

In the DNA constructs of the first and second systems, the specific gene and the reporter gene are preferably linked downstream of a promoter so that they can be expressed in multicellular organisms. The promoter is not particularly limited and can be appropriately selected depending on the application. Examples thereof include tissue-specific promoters such as unc-51, myo-2, myo-3, and dpy-7, developmental-stage specific promoters, and the like.

The DNA construct can be constructed by any method without limitation, and known techniques can be appropriately utilized. For example, the DNA construct can be constructed by integrating a reporter cassette, in which cDNA of the reporter gene is inserted into the genomic DNA fragment of the specific gene, into an expression vector that includes a desired promoter.

Hereinafter, various methods according to the present invention utilizing the first and second alternative splicing reporter systems will be described.

((1) Method for Detecting Alternative Splicing of a Specific Gene in a Multicellular Organism)

The method for detecting alternative splicing of a specific gene in a multicellular organism of the present invention comprises the steps of (a) introducing into the multicellular organism a DNA construct in the first system or a combination of DNA constructs in the second system (each contain the specific gene and the reporter gene), and (b) detecting the alternative splicing of the specific gene in the multicellular organism by detecting the expression of the reporter genes.

<Step (a)>

In the step (a), a DNA construct in the first system or a combination of DNA constructs in the second system is introduced into the multicellular organism to generate a transgenic multicellular organism. The DNA construct or the combination of DNA constructs can be introduced into the multicellular organisms by any method without limitation. For example, conventionally known techniques of gene transfer such as microinjection can be appropriately utilized.

<Step (b)>

In the step (b), alternative splicing of the specific gene in the multicellular organism is detected by detecting the expression of the reporter genes. Expression of the reporter genes can be detected by any method without limitation, and known detection methods can be appropriately utilized depending on the type of reporter gene. For example, when fluorescent proteins are used as the reporter, the expression can be detected using a fluorescence microscope or fluorescence-assisted worm sorter.

The DNA construct or the combination of DNA constructs contains at least two different reporter genes in total, and as described above, these reporter genes are inserted into the specific gene so that transcripts of the different reporter genes are fused with each of multiple mature mRNAs generated by alternative splicing. Therefore, by detecting the expression of these at least two different reporter genes in step (b), which form of mature mRNA is produced by alternative splicing can be checked; in other words, detection of alternative splicing patterns of the specific gene in vivo in multicellular organisms is made possible. The method for detecting alternative splicing of a specific gene in a multicellular organism also enables to detect tissue-specific and/or developmental stage-specific alternative splicing patterns in detail by changing the type of the promoter that is included in the DNA construct or the combination of DNA constructs, or changing developmental stage of the multicellular organism used.

((2) Method for Testing Whether or not a Compound to be Tested Affects Alternative Splicing of a Specific Gene)

The method for testing whether or not a compound to be tested affects alternative splicing of a specific gene of the present invention comprises the steps of (a) introducing into the multicellular organism a DNA construct in the first system or a combination of DNA constructs in the second system (each contain the specific gene and the reporter gene), (b) allowing the multicellular organism to contact the compound to be tested, (c) detecting the alternative splicing of the specific gene in the multicellular organism by detecting the expression of the reporter genes; and (d) determining whether or not the expression of the reporter genes detected in the (c) has changed compared to the expression of the reporter genes in a control which is not allowed to contact the compound to be tested.

<Step (a) and Step (c)>

The step (a) and the step (c) can be performed in the same manner as the step (a) and the step (b) in the "method for detecting alternative splicing of a specific gene in a multicellular organism" mentioned above, respectively.

<Step (b)>

In the step (b), the multicellular organism, into which the DNA construct or the combination of DNA constructs is introduced in the step (a), is allowed to contact a compound to be tested. The "compound to be tested" is not particularly limited and can be appropriately selected depending on the application from substances which one wants to test for whether or not they affect alternative splicing of the specific gene. Examples thereof include purified proteins, partially purified proteins, peptides, nonpeptidic compounds, artificially synthesized compounds, naturally-occurring compounds, and the like. In addition, the method for allowing the multicellular organism to contact the "compound to be tested" is not particularly limited; examples thereof include a method in which the "compound to be tested" is injected by microinjection, a method in which the "compound to be tested" is fed to the multicellular organism by mixing it in a food, and the like.

<Step (d)>

In the step (d), whether or not the expression of the reporter genes detected in the (c) has changed compared to the expression of the reporter genes in a control which is not allowed to contact the compound to be tested is determined. The change of the expression of the reporter genes is not particularly limited; examples thereof include replacement of the expression of one reporter gene with that of the other reporter gene, decrease or increase of the expression level of one reporter gene, and the like. If in step (d) it is determined that the expression of the reporter genes detected in step (c) has changed compared to the expression of the reporter genes in a control which is not allowed to contact the compound to be tested, it can be evaluated that the compound to be tested affects alternative splicing of the specific gene.

((3) Method for Identifying a Gene Region Affecting Alternative Splicing of a Specific Gene)

The method for identifying a gene region affecting alternative splicing of a specific gene of the present invention comprises the steps of (a) introducing into a multicellular organism a DNA construct in the first system, or a combination of DNA constructs in the second system (each contain the specific gene and the reporter gene), (b) treating the multicellular organism with a mutagen, (c) detecting the alternative splicing of the specific gene in the multicellular organism by detecting the expression of the reporter genes, (d) selecting an individual in which the expression of the reporter genes detected in step (c) has changed compared to the expression of the reporter genes in a control which is not subjected to the mutagen treatment, and (e) identifying a mutated gene region in the individual. The method allows the identification of trans-acting factors that affect alternative splicing of the specific gene.

<Step (a) and Step (c)>

The step (a) and the step (c) can be performed in the same manner as the step (a) and the step (b) in the "method for detecting alternative splicing of a specific gene in a multicellular organism" mentioned above, respectively.

<Step (b)>

In the step (b), the multicellular organism, into which the DNA construct or the combination of DNA constructs has been introduced in the step (a), is treated with a mutagen. The mutagen treatment of multicellular organisms is not particularly limited and can be performed by known methods. Examples thereof include treatment with ethyl methanesulfonate (EMS), treatment with ultraviolet light, and the like.

<Step (d)>

In the step (d), an individual, in which the expression of the reporter genes detected in step (c) has changed compared to the expression of the reporter genes in a control which is not subjected to the mutagen treatment, is selected. The change of the expression of the reporter genes is not particularly limited; examples thereof include replacement of the expression of one reporter gene with that of the other reporter gene, decrease or increase of the expression level of reporter gene, and the like.

<Step (e)>

In the step (e), a mutated gene region in the individual, in which the expression of the reporter genes has changed, is identified. The method for identifying the gene region is not particularly limited and conventionally known chromosome mapping and the like can be appropriately utilized. In the present invention, the present inventors identified a novel gene, "asd-1" which affects alternative splicing of egl-15 gene of *C. elegans*. The method for identifying the "asd-1" and details thereof are as described in Examples which will be described later.

((4) Method for Identifying a Region in a Specific Gene Affecting Alternative Splicing of the Specific Gene)

The method for identifying a region in a specific gene affecting alternative splicing of the specific gene of the present invention comprises steps of (a) introducing into the multicellular organism a DNA construct in the first system, or a combination of DNA constructs in the second system (each contain the specific gene and the reporter gene), wherein in the DNA construct or the combination of DNA constructs, a mutation has been introduced into the specific gene, (b) detecting the alternative splicing of the specific gene in the multicellular organism by detecting the expression of the reporter genes, and (c) determining whether or not the expression of the reporter genes detected in the (b) has changed compared to the expression of the reporter genes in a control in which a mutation has not been introduced into the specific gene. The method allows the identification of cis-acting DNA sequences that affect alternative splicing of the specific gene.

<Step (a)>

In the step (a), a DNA construct in the first system, or a combination of DNA constructs in the second system (each contain the specific gene and the reporter gene) is introduced into the multicellular organism, wherein in the DNA construct or the combination of DNA constructs, a mutation has been introduced into the specific gene. The method for introducing a mutation into the specific gene is not particularly limited and deletion, insertion, substitution, and the like can be appropriately induced in the specific gene by utilizing conventionally known techniques. In addition, the region in the specific gene into which a mutation is introduced is not particularly limited, and the region, for which one wants to evaluate whether the region affects alternative splicing of the specific gene, can be appropriately selected.

<Step (b)>

The step (b) can be performed in the same manner as the step (b) in the "method for detecting alternative splicing of a specific gene in a multicellular organism" mentioned above.

<Step (c)>

In the step (c), whether or not the expression of the reporter genes detected in the (b) has changed compared to the expression of the reporter genes in a control in which a mutation has not been introduced into the specific gene is determined. The change of the expression of the reporter genes is not particularly limited; examples thereof include replacement of the expression of one reporter gene with that of the other reporter gene, decrease or increase of the expression level of reporter gene, and the like. If it is determined that the expression of the reporter genes detected in the (b) has changed compared to the expression of the reporter genes in a control in which a mutation has not been introduced into the specific gene, the region in the specific gene into which a mutation is introduced can be identified as a region that affects alternative splicing of the specific gene. In the present invention, the present inventors identified UGCAUG sequence in the egl-15 gene of *C. elegans* as a region affecting alternative splicing of the gene. The method for identifying the "UGCAUG sequence" and details thereof are as described in Examples which will be described later.

The methods of the present invention: "(1) a method for detecting alternative splicing of a specific gene in a multicellular organism", "(2) a method for testing whether or not a compound to be tested affects alternative splicing of a specific gene", "(3) a method for identifying a gene region affecting alternative splicing of a specific gene", and "(4) a method for identifying a region in a specific gene affecting alternative splicing of the specific gene, which utilize the first and second alternative splicing reporter systems developed by the present inventors, can be a very useful way for the comprehensive study of regulation mechanisms of alternative splicing in multicellular organisms.

EXAMPLES

Examples of the present invention are illustrated below, but these are not to be construed as limiting the present invention.

Example 1

Generation of Transgenic Reporter Worms

As a model gene, the present inventors utilized egl-15, which encodes a sole homolog of fibroblast growth factor receptor (FGFR) in *C. elegans*. Its mutually exclusive exons 5A and 5B correspond to an insert within the extracellular domain (Goodman, S. J., Branda, C. S., Robinson, M. K., Burdine, R. D. & Stern, M. J. Alternative splicing affecting a novel domain in the *C. elegans* EGL-15 FGF receptor confers functional specificity. Development 130, 3757-3766 (2003).). EGL-15 (5B) and its ligand, LET-756/FGF, exert essential functions, while EGL-15 (5A) is specifically expressed in sex myoblasts, and is required for the directed migration of the cells towards EGL-17/FGF-releasing cells (Goodman, S. J., Branda, C. S., Robinson, M. K., Burdine, R. D. & Stern, M. J. Alternative splicing affecting a novel domain in the *C. elegans* EGL-15 FGF receptor confers functional specificity. Development 130, 3757-3766 (2003).).

In order to monitor the usage of mutually-exclusive exons, the present inventors first introduced cDNAs for RFP and GFP downstream of exon 5A and 5B, respectively, in separate mini-genes (FIG. 1A). When expressed under the unc-51 promoter, which drives expression in a variety of tissues, the transgenic worms showed differential expression patterns of GFP and RFP, corresponding to alternative splicing patterns (FIG. 1B).

Next, the present inventors constructed a unified reporter in which cDNAs for RFP and GFP were introduced into exons 5A- (E5A) and 5B-derived (E5B) exons, respectively (FIG. 2A). When expressed under the unc-51 promoter, the transgenic worms also showed a differential expression pattern of GFP and RFP (FIG. 2C), which was essentially the same pattern as FIG. 1B. The composition of mRNAs derived from the unified reporter transgene was consistent with the alternative selection of E5A and E5B (FIG. 2B), and predicted open reading frames (ORFs) corresponded to expression of RFP and GFP proteins, respectively (FIG. 2B). Consistent with the specific expression of endogenous exon 5A in sex myoblasts (Goodman, S. J., Branda, C. S., Robinson, M. K., Burdine, R. D. & Stern, M. J. Alternative splicing affecting a novel domain in the *C. elegans* EGL-15 FGF receptor confers functional specificity. Development 130, 3757-3766 (2003).), the vulval muscles, which derived from the sex myoblasts, exclusively expressed E5A-RFP (FIG. 2D). When the positions of cDNAs for GFP and RFP were interchanged in the reporter mini-gene (FIG. 2G), the expression patterns of GFP and RFP were completely reversed (compare panels C and D with H and I of FIG. 2), indicating that the tissue-dependent differential expression of GFP and RFP was not due to the differential stability of GFP- or RFP-containing mRNAs or proteins in different tissues. These results indicated that the transgenic egl-15 reporter worms enabled the monitoring of the expression profiles of alternative exons at a single cell level in vivo.

In order to analyze expression profiles of the egl-15 reporter, the present inventors generated several transgenic worms in which various tissue-specific promoters drove the expression of the reporter mini-gene. The myo-3 promoter predominantly drives the expression of E5A-RFP in body wall muscles (FIG. 2E) and vulval muscles (data not shown). E5B-GFP was exclusively expressed in the hypodermis under the dpy-7 promoter (FIG. 2F). When the positions of cDNAs for GFP and RFP were interchanged (FIG. 2G), the expression patterns of GFP and RFP were completely reversed (FIGS. 2J and K). These and other results are summarized in Table 1. These results indicated that the alternative splicing of egl-15 reporter was regulated in a tissue-dependent manner: muscular tissues predominantly express E5A, and the nervous system and epidermal tissues prefer E5B.

TABLE 1

| | Tissues | | | | | | | | |
|---|---|---|---|---|---|---|---|---|---|
| | Muscles | | | | Epidermis | | Nervous System | | |
| | | | | | | | | Mechano-sensory | |
| Promoter | Pharyngeal M. | Body Wall M. | Vulval M. | Anal M. | Hypodermis | Intestine | Amphid N. | N. | Motor N. |
| unc-51 | ■ | ■ | ■ | ■ | E5B | — | E5B > E5A | E5B > E5A | E5B > E5A |
| myo-2 | E5A = E5B | — | — | — | — | — | — | — | — |
| myo-3 | — | E5A = E5B | E5A = E5B | — | — | — | — | — | — |
| dpy-7 | — | — | — | — | E5B | — | — | — | — |
| elt-2 | — | — | — | — | — | E5B | — | — | — |
| F25B3.3 | — | — | — | — | — | — | E5B > E5A | E5B > E5A | E5B > E5A |

TABLE 1-continued

| | Tissues | | | | | | | | |
|---|---|---|---|---|---|---|---|---|---|
| | Muscles | | | | Epidermis | | Nervous System | | |
| | | | | | | | | Mechano- | |
| Promoter | Pharyngeal M. | Body Wall M. | Vulval M. | Anal M. | Hypodermis | Intestine | Amphid N. | sensory N. | Motor N. |
| mec-7 | — | — | — | — | — | — | — | E5B > E5A | — |
| unc-4 | — | — | — | — | — | — | — | — | E5B |

Expression of E5A and E5B was monitored by expression of fluorescent proteins from the transgenic reporters BGAR and/or BRAG driven under various promoters indicated.
E5A and E5B, exclusively expressing E5A and E5B, respectively.
E5A > E5B and E5B > E5A, predominantly expressing E5A and E5B, respectively.

FIGS. 1 and 2 will be specifically described below.

FIG. 1 depicts alternative splicing reporter worms with separate mini-genes (i.e., having a mini-gene in which cDNA for RFP is introduced downstream of exon 5A, and a mini-gene in which cDNA for GFP is introduced downstream of exon 5B). A, Schematic representation of egl-15 reporters E5AR (E5A-RFP) (top) and E5BG (E5B-GFP) (bottom), and schematic representation of mRNAs derived from each reporter mini-gene under the unc-51 promoter. Boxes indicate exons. Predicted open reading frames (ORFs) are colored in magenta for E5A-RFP, in green for E5B-GFP and in blue for others. B, Transgenic worms co-expressing E5AR and E5BG reporter under the unc-51 promoter. Projection images of E5A-RFP and E5B-GFP, merged and DIC images of the same field are shown. L3 larvae. Scale bar, 100 μm.

Methods: cDNAs for RFP and GFP were connected in frame to genomic fragments of egl-15 exon 4 through 5A and 4 through 5B, respectively. The composition of mRNAs was analyzed by cloning and sequencing RT-PCR products. Results: When co-expressed under the unc-51 promoter, which drives expression in a variety of tissues, transgenic worms showed differential expression patterns of GFP and RFP. Two forms of mRNAs were generated from each mini-gene. Intron 4 is retained in E4I4E5B, one form of mRNAs derived from the E5BG mini-gene. Notes: Expression of RFP- and GFP-fusion proteins reflected alternative selection of E5A and E5B, respectively. E4I4E5B was considered to correspond to the selection of E5A, since the absence E5A and suppression of E5B would result in the retention of intron 4.

FIG. 2 depicts alternative splicing reporter worms with unified mini-genes in which cDNAs for RFP and GFP were introduced downstream of exon 5A and upstream of exon 5B, respectively. A, Construction of egl-15 reporter BGAR (E5B-GFP/E5A-RFP). Genomic fragment of egl-15 exon 4 through 5A was amplified and cDNAs for GFP and RFP were inserted to construct the reporter cassette. The reporter cassette was introduced between promoter and 3' cassettes by homologous recombination. Boxes indicate exons. B, Schematic representation of mRNAs derived from the BGAR reporter in (A). Constitution of mRNAs was analyzed by cloning and sequencing RT-PCR products. Predicted open reading frames (ORFs) are colored in green for E5B-GFP and in magenta for E5A-RFP. *E5A denotes cryptic 3'-splice site within E5A. C to F, Transgenic worms expressing BGAR reporter under unc-51 (C and D), myo-3 (E) and dpy-7 (F) promoters. Projection images of E5A-RFP, E5B-GFP, merged and DIC images of the same fields are shown. G, Schematic representation of BRAG mini-genes. H to K, Merged views of confocal images of reporter worms expressing BRAG reporter under unc-51 (h, i), myo-3 (j) and dpy-7 (k) promoters. C, E, F, H, J, and K, L2-L3 larvae. D and I, Lateral view of an adult vulva. Scale bar in C, 100 μm for C, E, F, H, J, and K; in D, 50 μm for D and I.

Example 2

Screening for Mutants with Altered Expression Profiles

In order to examine the applicability of the transgenic reporter system constructed in Example 1 to elucidating regulation mechanisms of alternative splicing in vivo, the present inventors screened for mutants defective in the tissue-specific expression of the egl-15 reporter (FIG. 3A). The transgenic worms that predominantly expressed E5A-RFP in body wall muscles (FIG. 3C) were mutagenized, and those worms that expressed a higher level of GFP than the parental strain were isolated by utilizing a fluorescence-assisted worm sorter (FIG. 3B). Of approximately $5 \times 10^4$ genomes screened, the present inventors isolated 18 independent alleles with various expression profiles (FIGS. 3D to 3I). These mutants were classified according to their reporter expression profiles and SNP-based chromosome mapping (FIG. 3J). Two groups with the "Orange" phenotype expressed both E5B-GFP and E5A-RFP throughout the body wall muscles (FIGS. 3E and G) and were mapped to chromosome I. In another group with the "Chimera" phenotype, some body wall muscle cells predominantly expressed E5B-GFP, while other body wall muscle cells preferentially expressed E5A-RFP with a complementary pattern (FIG. 3D), and the gene was mapped to chromosome III. The other alleles showed chimeric expression profiles and were mapped to chromosome X (FIG. 3J). In one allele, E5B-GFP was predominantly expressed in most body wall muscle cells and a few expressed E5A-RFP (FIG. 3H); while in another, E5A-RFP-expressing cells predominated (FIG. 3I). The expression profiles were reproduced with 100% of penetrance in all these alleles. Altered profiles of alternative splicing were confirmed by RT-PCR analysis (FIG. 3K). These results demonstrate that our transgenic worms expressing an alternative splicing reporter, in combination with a fluorescence-assisted worm sorter, enable us to efficiently screen for splicing mutants.

FIG. 3 will be specifically described below.

FIG. 3 depicts screening for mutants defective in tissue-specific alternative splicing of egl-15 reporter. A, Schematic view of mutant screening. P0 hermaphrodite worms were treated with EMS and F2 worms were pooled and subjected to worm sorter screening. +, wild-type allele. m, mutant allele. B, An example of fluorescence profiles in mutant screening with a worm sorter. Each dot represents a single F2 worm. Worms (in a green triangle) that express more GFP than the parental strain were isolated. C to I, Confocal images of a parental and mutant strains. GFP in green and RFP in magenta. C, A parental strain ybIs736 [myo-3::EGL-15BGAR] X expressing the BGAR reporter in the body wall muscles under the myo-3 promoter. D to I, Mutant strains. Alleles are indicated. Scale bar, 100 μm. J, Summary of chromosome mapping. Genomic loci of all alleles examined are indicated. K, RT-PCR analysis of mRNAs derived from the reporter transgene. Top panel, egl-15 reporter; bottom panel, total RNAs prepared. Genetic backgrounds of ybIs736 reporter are indicated.

Example 3

Identification of asd-1 Gene

The present inventors identified a gene corresponding to the Chimera phenotype of the mutant screened in Example 2 (FIG. 3D). By sequencing genomic DNAs from the mutants, the present inventors identified mutations in a predicted gene, R74.5, from all seven alleles classified into the group, and we named the gene asd-1, for alternative-splicing-defective-1. ASD-1 protein has a single RNA recognition motif (RRM) and belongs to the evolutionarily conserved Fox-1 family (FIG. 4A). Vertebrates have three copies of family genes, and *Drosophila* has one. In *C. elegans*, FOX-1 (Skipper, M., Milne, C. A. & Hodgkin, J. Genetic and molecular analysis of fox-1, a numerator element involved in *Caenorhabditis elegans* primary sex determination. Genetics 151, 617-631 (1999).) and SPN-4 (Gomes, J. E. et al. The maternal gene spn-4 encodes a predicted RRM protein required for mitotic spindle orientation and cell fate patterning in early *C. elegans* embryos. Development 128, 4301-4314 (2001).) belong to the family. FIG. 4B shows the sequence alignment of the RRMs. The Fox-1 family has recently been identified as alternative splicing regulators with sequence-specific RNA binding properties (Jin, Y. et al. A vertebrate RNA-binding protein Fox-1 regulates tissue-specific splicing via the pentanucleotide GCAUG. Embo J 22, 905-912 (2003).), and structural analyses confirmed the binding specificity of the RRM of mammalian Fox-1/Fox-2 to UGCAUGU sequence (Auweter, S. D. et al. Molecular basis of RNA recognition by the human alternative splicing factor Fox-1. Embo J 25, 163-173 (2006).). The critical residues for recognition of the UGCAUG sequence are well conserved in the Fox-1 family, including ASD-1 and FOX-1 (FIG. 4B). Four alleles of the asd-1 mutants have nonsense mutations and three alleles have missense mutations within the conserved amino acid residues in the RRM (FIGS. 4A and B). All alleles in this group showed essentially the same phenotype. These results demonstrated that transgenic reporter worms allowed efficient mapping and identification of a gene causing altered alternative splicing.

The present inventors examined the genetic interaction between asd-1 and the other Fox-1 family genes. asd-1 and fox-1 had distinct but dosage-dependent effects on egl-15 reporter expression (FIGS. 4C to F): asd-1; fox-1 double homozygotes almost exclusively expressed E5B-GFP (FIG. 4F), while homozygotes in fox-1 alone were indistinguishable from wild-type background worms (FIGS. 4C and D), and heterozygotes of one gene in the homozygous background of the other showed an intermediate phenotype (FIGS. 4D and E). RT-PCR analysis confirmed the effects of asd-1 and fox-1 mutations on the splicing patterns of the egl-15 reporter (FIG. 4G). On the other hand, mutation in spn-4 did not affect egl-15 reporter expression, and spn-4 had no apparent genetic interaction with asd-1 and fox-1 (data not shown). These results indicate that asd-1 and fox-1 cooperatively regulate the egl-15 reporter in body wall muscles.

Figure 4:
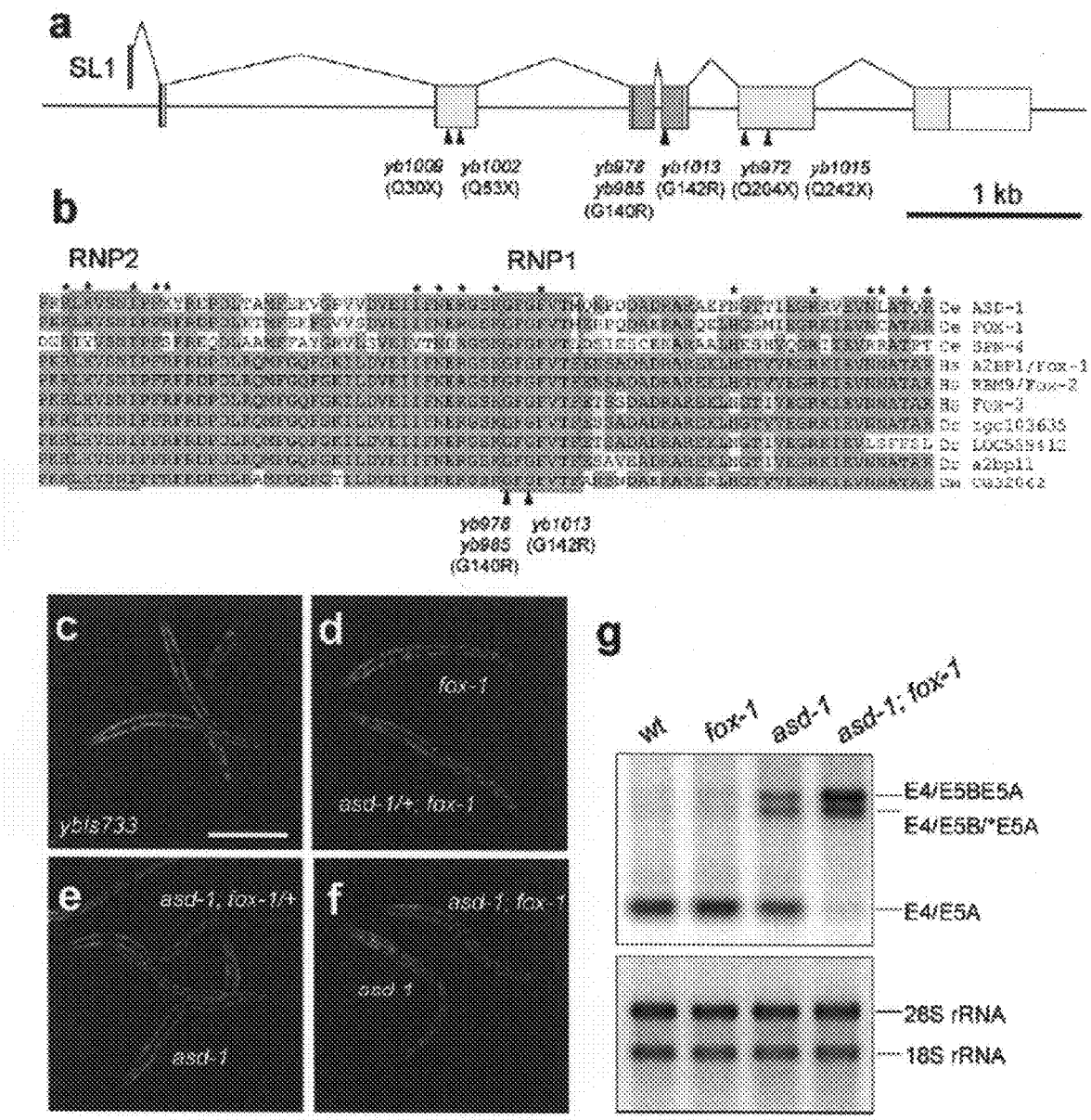
FIG. 4 depicts identification of asd-1 gene and genetic interaction between asd-1 and fox-1.

FIG. 4 will be specifically described below.

FIG. 4 depicts identification of asd-1 gene and genetic interaction between asd-1 and fox-1. A, Schematic representation of asd-1 gene and mutations identified in mutant alleles. Boxes indicate exons. ORF is in yellow and RNA recognition motif (RRM) in orange. SL1, a spliced leader. B, Amino acid sequence alignment of RRMs of Fox-1 family RNA-binding proteins in *C. elegans* (FOX-1, ASD-1 and SPN-4), mammals (A2BP1/Fox-1, RBM9/Fox-2 and LOC339162/D11Bwg0517e/Fox-3), zebrafish (zgc103635, LOC559412 and a2 bp11) and *Drosophila* (Dm CG32062). Conserved amino acid residues are shaded in orange and yellow. Conserved RNP1 and RNP2 motifs are boxed in green. Positions of missense mutations identified in asd-1 mutant alleles are indicated. C to F, Merged view of E5A-RFP and E5B-GFP of ybIs733 [myo-3::EGL-15BGAR] reporter with wild-type (C), fox-1 (e2643) and asd-1 (yb978)/+; fox-1 (D), asd-1 and asd-1; fox-1/+ (E) and asd-1 and asd-1; fox-1 (F) backgrounds. Scale bar, 100 μm. G, RT-PCR analysis of mRNAs derived from the BGAR reporter (top panel). Genetic backgrounds of ybIs733 reporter are indicated. Each band corresponds to mRNAs indicated in FIG. 2B. Bottom panel, total RNAs prepared.

Example 4

Regulation Mechanisms of the egl-15 Reporter

Figure 6:
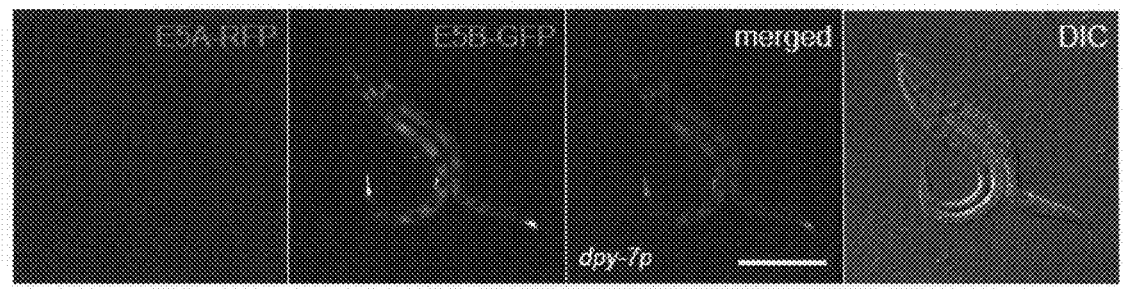
FIG. 6 shows that mutation in UGCAUG sequence does not affect E5B-GFP selection in hypodermis.
Figure 7:
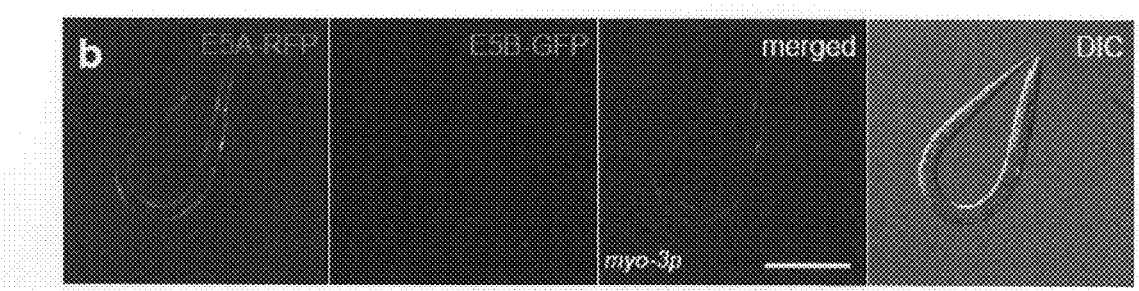
FIG. 7 shows that inactivation of E5B-GFP leads to selection of E5A-RFP even though UGCAUG sequence is mutagenized.

Next, the present inventors searched for a cis-element corresponding to asd-1 and fox-1 function by modifying the reporter mini-gene constructed in Example 1. Since vertebrate Fox-1 has been shown to specifically bind to a (U)GCAUG sequence (Jin, Y. et al. A vertebrate RNA-binding protein Fox-1 regulates tissue-specific splicing via the pentanucleotide GCAUG. Embo J 22, 905-912 (2003).) and a UGCAUG sequence is conserved in the 3' portion of egl-15 intron 4 in nematodes (FIG. 5A), the present inventors examined whether the UGCAUG sequence is involved in the regulation of egl-15 reporter. When a point mutation was introduced into the sequence of the reporter mini-gene (FIG. 5B), the expression of E5A-RFP was hardly detectable, and instead, the expression of E5B-GFP was enhanced in the body wall muscles (FIG. 5C), while the exclusive expression of E5B-GFP was not affected in the hypodermis (FIG. 6). These profiles suggested that the UGCAUG sequence is required for the suppression of E5B-GFP and/or the selection of E5A-RFP in the body wall muscles. To discriminate these possibilities, the present inventors further introduced mutations to inactivate the splicing acceptor site for E5B-GFP. In this case, E5A-RFP was expressed in the body wall muscles (FIG. 7). In the hypodermis, inactivation of the splicing acceptor site for E5B-GFP also resulted in the selection of E5A-RFP (FIG. 8). On the other hand, the deletion of the authentic E5B sequences did not affect the inclusion or suppression of E5B-GFP (FIG. 9). These results indicated that the UGCAUG sequence was required to suppress the selection of E5B-GFP and that E5A-RFP could be selected when upstream E5B-GFP was unavailable.

The present inventors then asked whether ASD-1 and FOX-1 proteins were able to directly bind to the UGCAUG sequence identified in the egl-15 intron 4 in vitro. As expected, both ASD-1 and FOX-1 proteins bound to an RNA probe derived from wild type intron 4, but not to an RNA probe with a mutation within the sequence (FIGS. 5D to 5H). Mutant ASD-1 proteins ASD-1(G140R) and ASD-1(G142R), derived from asd-1 mutant alleles, failed to bind to the RNA probes (FIGS. 5F to H), indicating that the binding was essential for ASD-1 function. From these results, the present inventors raise a model of regulation of the egl-15 alternative splicing reporter in body wall muscles (FIG. 5I). In the wildtype background, ASD-1 and FOX-1 bind to the UGCAUG sequence in intron 4 to suppress the selection of E5B-GFP, thereby enhancing the selection of E5A-RFP. When ASD-1 and FOX-1 are absent or the UGCAUG sequence is mutagenized, the cis-element is not occupied and upstream E5B-GFP is preferably selected. When E5B-GFP is unavailable because of a mutation in the splicing acceptor site, downstream E5A-RFP can be selected.

FIGS. 5 to 9 will be specifically described below.

Figure 5:
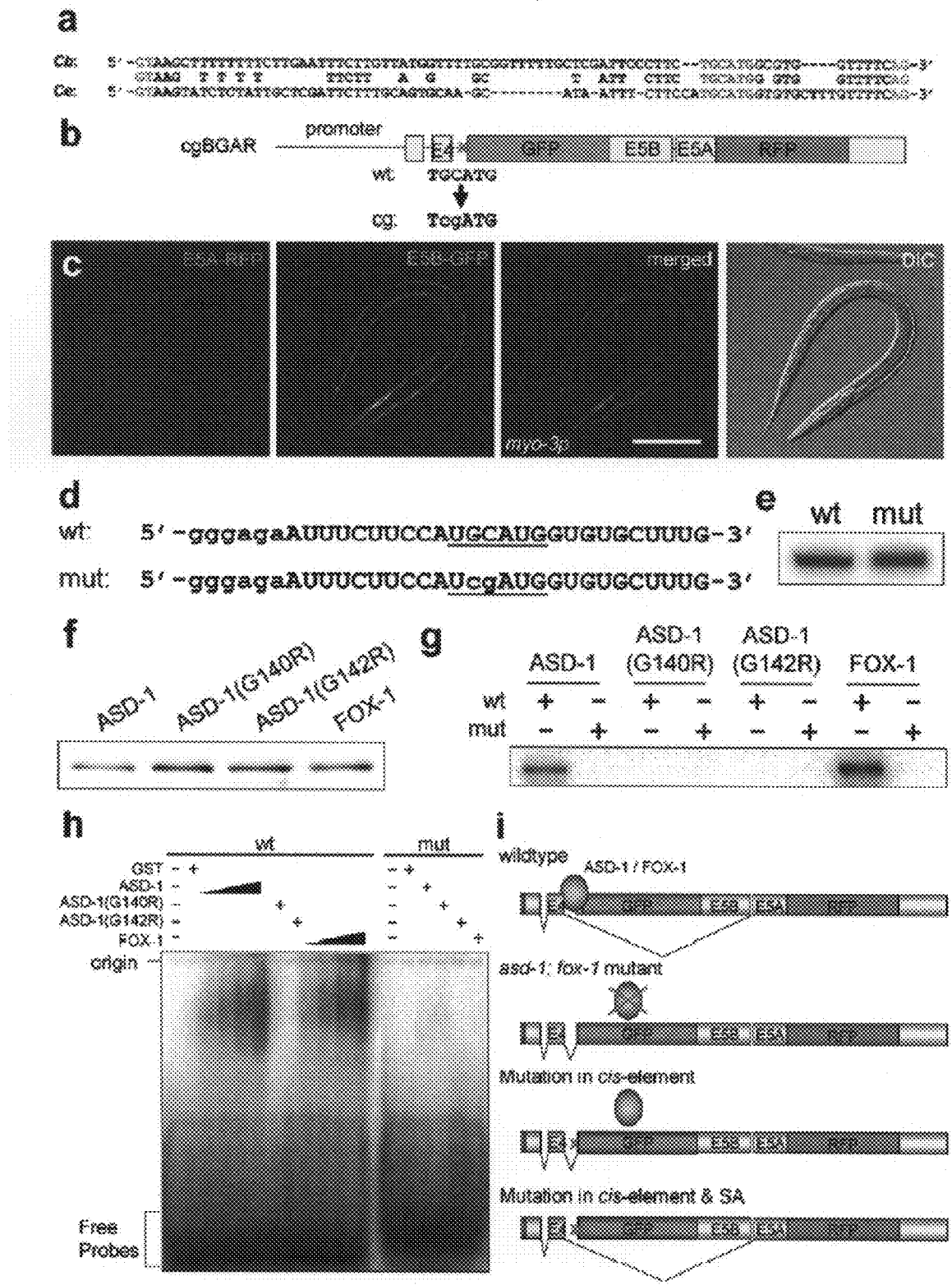
FIG. 5 depicts regulation mechanisms of alternative splicing of egl-15 reporter in body wall muscles.

FIG. 5 depicts regulation mechanisms of alternative splicing of egl-15 reporter in body wall muscles. A, Nucleotide sequence alignment of egl-15 intron 4 from *C. briggsae* (Cb) and *C. elegans* (Ce). Conserved nucleotides are indicated between the two sequences. The UGCAUG sequence is colored in magenta. Conserved dinucleotides in splice donor and acceptor sites are in green. B, Schematic representation of cgBGAR mini-genes. TGCATG sequence in intron 4 is mutagenized to TcgATG. C, Transgenic worms expressing cgBGAR reporter under myo-3 promoter. Scale bar, 100 μm. D, Sequences of wildtype (wt) and mutant (mut) RNA probes used in the in vitro RNA-binding assays. Uppercase letters indicate sequences derived from egl-15 intron 4. The UGCAUG sequence is underlined. E, Radioisotope-labeled RNA probes used in the assays. RNA probes were electrophoresed in a denaturing condition and autoradiographed. F, Recombinant proteins used in the assays. Recombinant GST-fusion proteins were electrophoresed and detected with an anti-GST antibody. G, UV-crosslinking assay. Recombinant proteins and RNA probes used are indicated. H, Electophoretic mobility shift assay. RNA probes and recombinant proteins used are indicated. Two-fold dilution series of ASD-1 and FOX-1 proteins were used. I, Schematic model of tissue-specific regulation of egl-15 reporters in body wall muscles. Details were described above.

FIG. 6 shows that mutation in UGCAUG sequence does not affect E5B-GFP selection in hypodermis. Transgenic worms expressing cgBGAR reporter under the dpy-7 promoter are shown. Scale bar, 100 μm. Note that this expression pattern is indistinguishable from that in FIG. 2F.

FIG. 7 shows that inactivation of E5B-GFP leads to selection of E5A-RFP even though UGCAUG sequence is mutagenized. A, Schematic representation of the cgttBGAR mini-gene. Splice acceptor (SA) site of E5B-GFP is mutagenized from AG to TT in addition to mutation of TGCATG sequence in intron 4 into TcgATG. B, Transgenic worms expressing cgttBGAR reporter under the myo-3 promoter. Scale bar, 100 μm.

FIG. 8 shows that inactivation of E5B-GFP leads to selection of E5A-RFP in hypodermis. A, Schematic representation of the ttBGAR mini-gene. Splice acceptor (SA) site of E5B-GFP is mutagenized from AG to TT. B, Transgenic worms expressing ttBGAR reporter under the dpy-7 promoter. Scale bar, 100 μm. Note that compared to the expression pattern in FIG. 2F, E5B-GFP has almost disappeared and E5A-RFP is detected instead.

FIG. 9 shows that exon 5B sequence is not required for inclusion or suppression of E5B-GFP. A, Schematic representation of egl-15 reporters Δ200BGAR (top) and Δ300BGAR (bottom), and schematic representation of major forms of mRNAs derived from each reporter under the unc-51 promoter. Boxes indicate exons. Predicted ORFs are colored in magenta for E5A-RFP, in green for E5B-GFP and in blue for others. *E5A denotes cryptic 3'-splice site within E5A. B and C, Transgenic worms expressing Δ200BGAR (B) and Δ300BGAR (C) reporters under the unc-51 promoter. Projection images of E5A-RFP and E5B-GFP, merged and DIC images of the same fields are shown. L2-L3 larvae. Scale bar, 100 μm.

Methods: Exonic sequences in E5B of the BGAR mini-gene (FIG. 2A) were deleted in these mini-genes. Out of 300-bp of the authentic exon 5B sequence used in the BGAR mini-gene, 94-bp and 6-bp of 3' portions were left in Δ200BGAR and Δ300BGAR, respectively. The composition of mRNAs was analyzed by cloning and sequencing RT-PCR products. Results: Expression of E5B-GFP was not affected in either of the reporters, while the expression of E5A-RFP was diminished in the Δ300BGAR reporter worm. Three/two forms of mRNAs were predominantly generated from each mini-gene. Intron 4 and E5B-GFP were retained in E4I4E5BE5A from the Δ300BGAR reporter. Notes: Alternative forms of mRNAs from the reporter mini-genes reflected alternative selection of E5A and E5B. E4I4E5BE5A was considered to correspond to the selection of E5A; deletion near the splice acceptor site for E5A may have prevented the authentic splicing to E5A, resulting in the retention of intron 4. E5B-GFP was either included or suppressed even when most of the authentic exon 5B was deleted.

Example 5 asd-1 and fox-1 Regulate Endogenous egl-15 Gene

Lastly, the present inventors examined whether their model, that the selection of egl-15 exon 5A depends on asd-1/fox-1 function, could be applied to the endogenous egl-15 gene. RT-PCR analysis revealed that the amount of endogenous egl-15 mRNA isoforms including exon 5A was indeed reduced in the double mutant (FIG. 10A). Mutations within egl-15 exon 5A have been shown to cause the aberrant migration of the sex myoblasts leading to the Egg-laying-defective (Egl) phenotype (Goodman, S. J., Branda, C. S., Robinson, M. K., Burdine, R. D. & Stern, M. J. Alternative splicing affecting a novel domain in the *C. elegans* EGL-15 FGF receptor confers functional specificity. Development 130, 3757-3766 (2003).). The present inventors found that the asd-1; fox-1 double mutant was also Egl: with a much smaller number of embryos on the culture plates (data not shown) and the presence of late stage embryos in the uterus (FIGS. 10B, C). Further, the vulval muscles were off the vulva in the double mutant (FIG. 10B to E). These results indicated that asd-1; fox-1 double mutants phenocopied the specific loss of function of EGL-15 (5A) isoforms and that asd-1 and fox-1 were redundantly required for the selection of endogenous egl-15 exon 5A in sex myoblasts (FIG. 11). The transgenic reporters can thus be utilized to elucidate regulation mechanisms of alternative splicing of endogenous genes in vivo.

Figure 10:
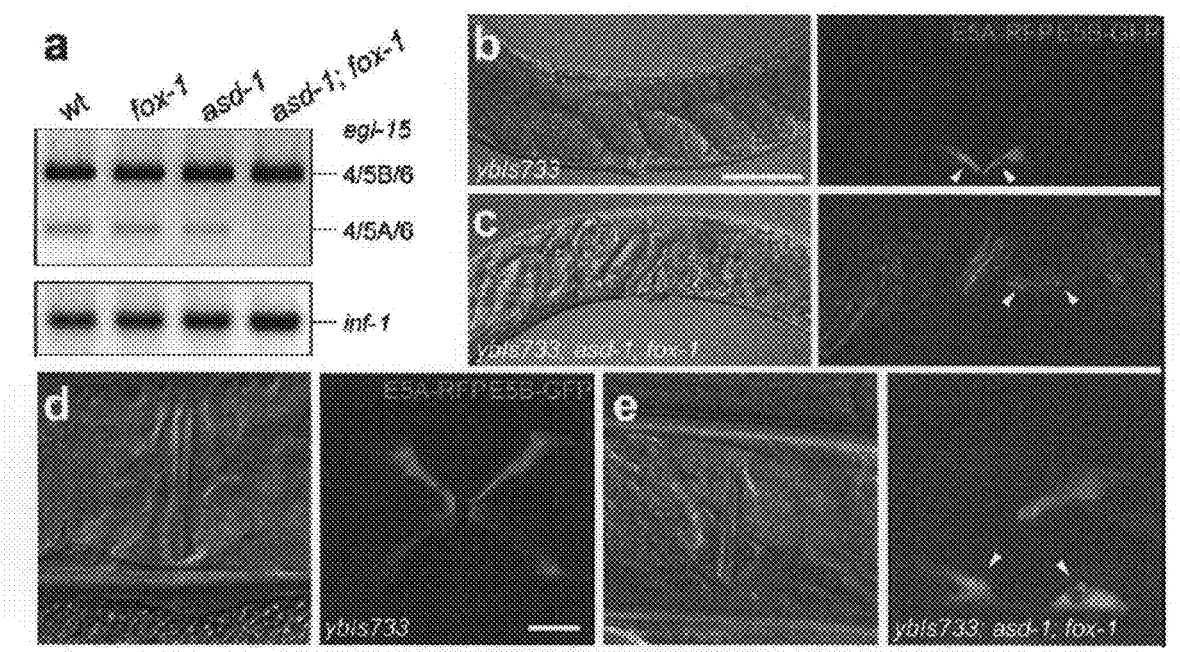
FIG. 10 shows regulation of the endogenous egl-15 exon 5s by asd-1 and fox-1.

FIGS. 10 and 11 will be specifically described below.

FIG. 10 shows regulation of the endogenous egl-15 exon 5s by asd-1 and fox-1. A, RT-PCR analyses of endogenous egl-15 (upper panel). Genetic backgrounds of the ybIs733 reporter are indicated. Lower panel, inf-1 was used as a reaction control. B-E, DIC images and merged confocal images of ybIs733 reporter worms (B, D) and asd-1; fox-1; ybIs733 (C, E). Lateral views of gravid adult hermaphrodites (B, C) and magnified ventral views of the vulva (D, E). Arrowheads indicate vulval muscles. Anterior is to the left. Scale bar in B, 50 μm; in D, 10 μm.

FIG. 11 is a diagram showing a model of regulation of endogenous egl-15 exon 5s in sex myoblasts. Top panel, in wild-type worms, ASD-1 and FOX-1 binds to the UGCAUG sequence in intron 4 to suppress selection of exon 5B and therefore downstream exon 5A is selected. Bottom panel, in the asd-1; fox-1double mutant, the UGCAUG sequence in intron 4 is not occupied and upstream exon 5B is preferred.

[Methods]

In Examples 1 to 5, plasmid construction, worm culture, and in vitro binding assays were each performed as follows.

—Plasmid Construction—

Reporter mini-genes were constructed essentially as described in FIG. 2A. Primers used to amplify egl-15 genomic fragments are 5'-GTCTCTAGACGTACACAACG-CATCTGGACA-3' (SEQ ID NO:1), 5'-CAAAGATCT-GAAAACAAAGCACACCATSSATGG-3' (SEQ ID NO:2), 5'-TGAAGCGGCCGCTGGAATGTGTTTGTTTAT-3' (SEQ ID NO:3) and 5'-GCGGATCCAAAGGATGAT-TGATCTGTCTTA-3' (SEQ ID NO:4). Mutations were introduced by utilizing QuickChange (Stratagene). Promoter vectors were constructed as Gateway Destination vectors (Invitrogen) modified from pPD49.26 (gift of A. Fire). Nucleotide sequences of promoter vectors are available on the *C. elegans* promoter database (http://www.shigen.nig.ac.jp/c.elegans/promoter/index.jsp). Expression vectors were constructed by homologous recombination between reporter cassettes and promoter vectors. GFP cDNA was derived from pEGFP-N2 (Clontech) and RFP cDNA was derived from mRFP1 (gift of R. Y. Tsien).

—Worm Culture and Microscopy—

Worms were cultured following standard methods. Transgenic lines were prepared by using lin-15 (n765) as a host. Integrant lines were generated by UV-irradiation (Mitani, S. Genetic regulation of mec-3 gene expression implicated in the specification of the mechanosensory neuron cell types in *Caenorhabditis elegans*. Dev. Growth & Diff. 37, 551-557 (1995).). EMS (ethyl methanesulfonate) mutagenesis was performed as described (Hodgkin, J. Conventional genetics. in *C. elegans* A PRACTICAL APPROACH (ed. Hope, I. A.) 245-270 (OXFORD, New York, 1999).). Mutants were screened by utilizing a fluorescence-assisted worm sorter, COPAS BIOSORT (Union Biometrica). Snip-SNPs mapping was performed as described (Wicks, S. R., Yeh, R. T., Gish, W. R., Waterston, R. H. & Plasterk, R. H. Rapid gene mapping in *Caenorhabditis elegans* using a high density polymorphism map. Nat Genet. 28, 160-164 (2001).). A confocal microscope, Fluoview FV500 (Olympus), was used for image scanning and acquired images were processed with Metamorph (Molecular Devices).

—In Vitro Binding Assays—

Recombinant proteins were produced as GST-fusion proteins by induction with L-arabinose in *E. coli* strain BL21-AI (Invitrogen). GST-fusion proteins were purified with Glutathione-Sepharose 4B (Pharmacia) and dialysed against RNA-binding buffer (200 mM KCl in HEPES-KOH (pH 7.9) with 1 mM DTT and 10 mM PMSF). RNA probes were synthesized by in vitro transcription with [$\alpha^{32}$P]UTP. In vitro binding experiments were performed in the presence of 130 ng/μl *E. coli* tRNA in 25 μl of RNA binding buffer for 30 min at 20° C. UV-crosslinking was performed by irradiating 18,000 J/m$^2$ of ultraviolet light with a crosslinker CL-1000 (UVP). The electrophoretic mobility shift assay was performed essentially as described (Jin, Y. et al. A vertebrate RNA-binding protein Fox-1 regulates tissue-specific splicing via the pentanucleotide GCAUG. Embo J 22, 905-912 (2003).) with 5% polyacrylamide gel and 0.5×TBE.

[Discussion]

The present inventors generated alternative splicing reporter worms that enabled to profile the expression patterns at the single cell level in vivo. The egl-15 reporter showed the differential expression profiles in various tissues, presumably reflecting intrinsic nature of each cell or "cellular codes". Complete penetrance of expression patterns of the egl-15 reporters in wildtype and mutant worms suggests the presence of strict regulation mechanisms in vivo. The present inventors demonstrated efficient identification of trans-acting factors, ASD-1 and FOX-1, and a cis-element, UGCAUG sequence, by utilizing the tissue-specific expression profiles of the egl-15 reporter. Both the egl-15 reporter and the endogenous egl-15 gene were redundantly regulated by asd-1 and fox-1 in vivo. It should be noted that the reporter expression profile was dependent on the dosage of the asd-1 and fox-1 genes, while asd-1 and fox-1 single mutants themselves were phenotypically normal. These facts emphasize that this transgenic reporter system enabled identification of asd-1 and fox-1 as redundant regulators of endogenous egl-15, which would not be achieved by conventional genetic screening of Egl mutants. The high sensitivity of the reporter, however, may lead to identification of trans-acting factors or signalling molecules that are not necessarily involved in the regulation of endogenous genes. It is critical to confirm that the endogenous genes are also regulated in the same manner. Utilization of the splicing mutants may facilitate the experimental validation of the regulator/target relation in vivo. The mutants will also allow global search for candidate target genes by utilizing whole-genome tiling arrays. Further collection and profiling of reporters based on other genes may lead to comprehensive spatiotemporal characterization of alternative splicing events in the organism.

In generating transgenic alternative-splicing reporters, the present inventors assumed that *C. elegans* is an appropriate model organism to generate in vivo reporter system. Most of the worm genes have multiple exons (Sakharkar, M. K. & Kangueane, P. Genome SEGE: a database for 'intronless' genes in eukaryotic genomes. BMC Bioinformatics 5, 67 (2004).). The average size of worm introns (267 bp) is comparable to that of internal exons (218 bp), which is in great contrast to those in human (>3,300 bp versus 145 bp) (Lander, E. S. et al. Initial sequencing and analysis of the human genome. Nature 409, 860-921 (2001).). Furthermore, larger internal exons of several hundred base pairs are frequently found in *C. elegans* (Lander, E. S. et al. Initial sequencing and analysis of the human genome. Nature 409, 860-921 (2001).). These facts lead us to assume that exonic elements would be less essential for the splicing machinery to define exons in pre-mRNAs and insertion of GFP/RFP cDNA in internal exons would have less effect on the authentic splicing in *C. elegans* than in vertebrates. The present inventors investigated various forms of the transgenic reporters for the egl-15 exon 5s: with the separate mini-genes (FIG. 1) and with the unified mini-genes (FIGS. 2 and 9). These reporters showed essentially the same tissue-specific expression profiles of GFP/RFP proteins and the experimentally confirmed splicing patterns of mRNAs corresponded to the alternative selection of E5s. These results verified our assumption that the insertion of the GFP/RFP cDNA into internal E5B or the deletion of the authentic exon 5B sequence did not affect the inclusion or suppression of E5B in the egl-15 reporters. Further analyses lead us to the model that binding of trans-acting factors to the intron 4 determines whether to include or suppress the exon 5B (FIG. 11). However, the position of the essential cis-elements cannot always be applied to other mutually exclusive alternative splicing events, since the present inventors encountered a case in which a downstream intron is essential for the regulated expression of mutually exclusive exons (H. K., unpublished observation). Therefore, it is critical for constructing splicing reporters that the expression of GFP and RFP proteins directly reflects either of the alternative splicing events and that expression profiles of the reporter corresponds to that of the endogenous genes.

The Fox-1 families regulate alternative splicing by binding to a UGCAUG sequence with extraordinarily high sequence specificity compared to other trans-acting RNA binding proteins. The present inventors demonstrated the first genetic evidence that the Fox-1 family regulates tissue-specific mutually exclusive alternative splicing of an endogenous gene in vivo via specific binding to a UGCAUG sequence in a dose-dependent manner. egl-15 encodes FGFR and alternate usage of exon 5s determines ligand specificity (Goodman, S. J., Branda, C. S., Robinson, M. K., Burdine, R. D. & Stern, M. J. Alternative splicing affecting a novel domain in the C. elegans EGL-15 FGF receptor confers functional specificity. Development 130, 3757-3766 (2003).). One of the mammalian counterparts of egl-15 gene, FGFR2, also has tissue-specific mutually exclusive exons IIIb and IIIc and these exons ultimately confer ligand specificity (Dell, K. R. & Williams, L. T. A novel form of fibroblast growth factor receptor 2. Alternative splicing of the third immunoglobulin-like domain confers ligand binding specificity. J Biol Chem 267, 21225-21229 (1992).). A recent report showed that the expression of Fox-2/RBM9 in cultured cells regulated the transition from FGFR2(IIIc) to FGFR2(IIIb) by binding to UGCAUG sequences (Baraniak, A. P., Chen, J. R. & Garcia-Blanco, M. A. Fox-2 mediates epithelial cell-specific fibroblast growth factor receptor 2 exon choice. Mol Cell Biol 26, 1209-1222 (2006).). These correlations between C. elegans and mammals suggest that Fox-1/UGCAUG-mediated regulation is an evolutionarily conserved mechanism to determine tissue-specific alternative splicing patterns in metazoans. The consequences of Fox-1/UGCAUG interaction, however, seem to be more complicated. In the case of egl-15 exon 5s, the binding of FOX-1/ASD-1 to a single UGCAUG sequence in intron 4 suppresses the selection of exon 5B, leading to the selection of downstream exon 5A. In the same way, in cultured cells, vertebrate Fox-1 suppressed the inclusion of mitochondrial ATP synthase Fly exon 9 and non-muscle exon of α-actinin gene by binding to UGCAUG sequences within the upstream intron (Jin, Y. et al. A vertebrate RNA-binding protein Fox-1 regulates tissue-specific splicing via the pentanucleotide GCAUG. Embo J 22, 905-912 (2003).). On the other hand, vertebrate Fox-1 or Fox-2 can induce the inclusion of fibronectin EIIIB exon (Jin, Y. et al. A vertebrate RNA-binding protein Fox-1 regulates tissue-specific splicing via the pentanucleotide GCAUG. Embo J 22, 905-912 (2003).), FGFR2 exon IIb (Baraniak, A. P., Chen, J. R. & Garcia-Blanco, M. A. Fox-2 mediates epithelial cell-specific fibroblast growth factor receptor 2 exon choice. Mol Cell Biol 26, 1209-1222 (2006).) and neuron-specific c-src N1 exon (Nakahata, S. & Kawamoto, S. Tissue-dependent isoforms of mammalian Fox-1 homologs are associated with tissue-specific splicing activities. Nucleic Acids Res 33, 2078-2089 (2005).; Underwood, J. G., Boutz, P. L., Dougherty, J. D., Stoilov, P. & Black, D. L. Homologues of the Caenorhabditis elegans Fox-1 protein are neuronal splicing regulators in mammals. Mol Cell Biol 25, 10005-10016 (2005).) by binding to UGCAUG sequences within the downstream intron. The differential effect of Fox-1/UGCAUG interaction may depend on relative positions of the sequences (Underwood, J. G., Boutz, P. L., Dougherty, J. D., Stoilov, P. & Black, D. L. Homologues of the Caenorhabditis elegans Fox-1 protein are neuronal splicing regulators in mammals. Mol Cell Biol 25, 10005-10016 (2005).). Furthermore, A2 bp1/Fox-1 and Rbm9/Fox-2 genes have multiple promoters and multiple alternative exons, and these isoforms showed differential subcellular localization and effects on alternative splicing events (Nakahata, S. & Kawamoto, S. Tissue-dependent isoforms of mammalian Fox-1 homologs are associated with tissue-specific splicing activities. Nucleic Acids Res 33, 2078-2089 (2005).; Underwood, J. G., Boutz, P. L., Dougherty, J. D., Stoilov, P. & Black, D. L. Homologues of the Caenorhabditis elegans Fox-1 protein are neuronal splicing regulators in mammals. Mol Cell Biol 25, 10005-10016 (2005).), suggesting complicated regulation of Fox-1/UGCAUG-mediated alternative splicing. Existence of mutants with various types of egl-15 reporter expression profiles shown in FIGS. 3D to I suggests that several unidentified genes are involved in the regulation of the egl-15 reporter. Identification of these genes would lead to further understanding of selection mechanisms of egl-15 exon 5s and/or regulation of asd-1/fox-1 function in vivo. Since C. elegans has relatively small introns and the regulation mechanisms are expected to be simple, this transgenic reporter worm system may help to understand basic rules of alternative splicing regulation in higher eukaryotes.

What is claimed is:

1. A method for testing whether or not a compound to be tested affects an alternative splicing of a specific gene, the method comprising:
   (a) introducing into a nematode a DNA construct such that at least two different reporter genes are inserted into the specific gene which undergoes the alternative splicing, wherein the reporter genes are inserted so that transcripts of the different reporter genes are each fused with each of at least two different mature mRNAs generated by the alternative splicing;
   (b) allowing the nematode to contact the compound to be tested;
   (c) detecting the alternative splicing of the specific gene in the nematode by the expression of the reporter genes; and
   (d) determining whether or not the expression of the reporter genes detected in the (c) has changed compared to the expression of the reporter genes in a control which is not allowed to contact the compound to be tested.

2. A method for testing whether or not a compound to be tested affects an alternative splicing of a specific gene, the method comprising:
   (a) introducing into a nematode a combination of DNA constructs,
   wherein in the DNA construct, a reporter gene is inserted into the specific gene which undergoes the alternative splicing, and the combination of DNA constructs satisfies all of the following conditions (i) to (iv):
   (i) reporter genes inserted into each DNA construct are different from each other,
   (ii) in each DNA construct, the reporter gene is inserted into the specific gene so that a transcript of the reporter gene is fused with a plurality of mature mRNAs generated by the alternative splicing,
   (iii) a transcript portion of the reporter gene in only one mature mRNA of the plurality of mature mRNAs generated by the alternative splicing from each DNA construct is translated in a correct reading frame, and
   (iv) only when a specific splicing is selected among alternative splicing patterns, the translation in a correct reading frame is induced in each DNA construct, and the specific splicing which induces the translation in a correct reading frame is different depending on each DNA construct;
   (b) allowing the nematode to contact the compound to be tested;
   (c) detecting the alternative splicing of the specific gene in the nematode by the expression of the reporter genes; and
   (d) determining whether or not the expression of the reporter genes detected in the (c) has changed compared to the expression of the reporter genes in a control which is not allowed to contact the compound to be tested.

3. The method according to either claim 1 or claim 2, wherein each of at least two different reporter genes is connected to a different exon which is included in a different transcript as a result of the alternative splicing.

4. The method according to either claim 1 or claim 2, wherein the specific gene is linked to a promoter so that the specific gene functions under the control of the promoter, wherein the promoter is one of a tissue-specific promoter and a developmental stage-specific promoter.

5. The method according to either claim 1 or claim 2, wherein the nematode is a C. elegans.

6. The method according to either claim 1 or claim 2, wherein the specific gene is egl-15.

7. The method according to either claim 1 or claim 2, wherein the reporter genes are a gene encoding a fluorescent protein.

8. The method according to claim 7, wherein the expression of the reporter genes is detected using a worm sorter.

* * * * *